(12) United States Patent
Davis et al.

(10) Patent No.: US 6,316,687 B1
(45) Date of Patent: Nov. 13, 2001

(54) DISPOSABLE DIAPER HAVING A HUMIDITY TRANSFER REGION, BREATHABLE ZONE PANEL AND SEPARATION LAYER

(75) Inventors: James Arthur Davis, Roswell, GA (US); Karen Marie Arnold, Neenah, WI (US); Mary Beth Eckhardt, Cedar Hill, TX (US); Rebecca Jean Kuepper; Pamela Jean Mayberry, both of Appleton, WI (US); Michael Tod Morman, Alpharetta, GA (US); Thomas Walter Odorzynski, Green Bay; MaryAnn Zunker, Oshkosk, both of WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 08/085,462

(22) Filed: Jun. 30, 1993

Related U.S. Application Data

(63) Continuation of application No. 07/573,861, filed on Aug. 30, 1990, now abandoned, which is a continuation-in-part of application No. 07/416,897, filed on Oct. 4, 1989, now abandoned.

(51) Int. Cl.[7] ............................. A61F 13/15; A61F 13/20
(52) U.S. Cl. ..................... 604/372; 604/378; 604/385.01
(58) Field of Search ................................... 604/368, 376, 604/372, 373, 378, 381–384, 385.1, 385.2, 385.01, 385.13, 385.3

(56) References Cited

U.S. PATENT DOCUMENTS

| | | |
|---|---|---|
| 2,544,069 | 3/1951 | Cutler . |
| 3,081,772 | 3/1963 | Brooks et al. . |
| 3,592,194 | 7/1971 | Duncan . |

(List continued on next page.)

FOREIGN PATENT DOCUMENTS

| | | |
|---|---|---|
| 8520621 | 8/1985 | (DE) . |
| 3525379 | 1/1987 | (DE) . |
| 3319043 | * 11/1984 | (DE) ................................. 604/358 |
| 0165807 | 12/1985 | (EP) . |
| 0174775 | 3/1986 | (EP) . |
| 0193309 | 9/1986 | (EP) . |
| 0269401 | 1/1988 | (EP) . |
| 0269401 | 6/1988 | (EP) . |
| 0323634 | 7/1989 | (EP) . |
| 0456885 | 11/1991 | (EP) . |
| 2023068 | 12/1979 | (GB) . |
| 2055586 | 3/1981 | (GB) . |
| 2101038 | 1/1983 | (GB) . |
| 2115702 | 9/1983 | (GB) . |
| 2145661 | 4/1985 | (GB) . |
| 2170108 | 7/1986 | (GB) . |
| 2171915 | 9/1986 | (GB) . |
| 2193625 | 2/1988 | (GB) . |
| 2242610 | 10/1991 | (GB) . |
| 2244422 | 12/1991 | (GB) . |
| 61-2854 | 1/1986 | (JP) . |
| 85/00157 | 9/1986 | (WO) . |

*Primary Examiner*—John G. Weiss
*Assistant Examiner*—K. M. Reichle
(74) *Attorney, Agent, or Firm*—Paul Yee

(57) ABSTRACT

A distinctive absorbent garment article generally delimits a front waistband section, a rear waistband section and an intermediate section which interconnects the front and rear waistband sections. The article has a substantially fluid-impermeable backsheet layer, a liquid permeable topsheet layer, positioned in facing relation with the backsheet layer, and an absorbent body located between the backsheet layer and topsheet layer. The absorbent body includes a distinctive humidity transfer region which is advantageously configured to exhibit relatively low moisture retention. A vapor permeable panel is connected to the backsheet layer at one or more waistband sections of the article, and is arranged in an overlying registry with the humidity transfer region of the absorbent body.

69 Claims, 15 Drawing Sheets

U.S. PATENT DOCUMENTS

| | | | | |
|---|---|---|---|---|
| 3,595,235 | | 7/1971 | Jespersen . | |
| 3,665,921 | | 5/1972 | Stumpf . | |
| 3,871,378 | | 3/1975 | Duncan et al. . | |
| 3,927,673 | * | 12/1975 | Taylor | 604/384 |
| 3,945,386 | | 3/1976 | Anczuroweski et al. . | |
| 3,965,906 | | 6/1976 | Karami . | |
| 3,987,792 | | 10/1976 | Hernandez et al. . | |
| 4,014,341 | | 3/1977 | Karami . | |
| 4,041,951 | | 8/1977 | Sanford . | |
| 4,077,410 | | 3/1978 | Butterworth et al. . | |
| 4,232,674 | | 11/1980 | Melican . | |
| 4,259,958 | | 4/1981 | Goodbar . | |
| 4,285,342 | | 8/1981 | Mesek . | |
| 4,304,234 | | 12/1981 | Hartmann . | |
| 4,306,559 | * | 12/1981 | Nishzawa et al. | 604/383 |
| 4,324,247 | | 4/1982 | Aziz . | |
| 4,338,371 | | 7/1982 | Dawn et al. . | |
| 4,341,216 | * | 7/1982 | Obenour | 604/381 |
| 4,372,312 | | 2/1983 | Fendler et al. . | |
| 4,381,611 | | 5/1983 | Wishman | 34/9 |
| 4,381,782 | | 5/1983 | Mazurake tal. | 604/368 |
| 4,392,861 | | 7/1983 | Butterworth et al. | 604/366 |
| 4,405,325 | | 9/1983 | Antlfinger et al. | 604/370 |
| 4,413,032 | | 11/1983 | Hartmann et al. | 428/288 |
| 4,421,813 | | 12/1983 | Athey | 428/195 |
| 4,428,128 | * | 1/1984 | Motomura | 604/384 |
| 4,436,780 | | 3/1984 | Hotchkiss et al. | 428/198 |
| 4,480,000 | | 10/1984 | Watanabe et al. | 428/284 |
| 4,500,315 | | 2/1985 | Pienaik et al. | 604/379 |
| 4,519,798 | | 5/1985 | Dinius | 604/358 |
| 4,519,799 | | 5/1985 | Sakurai et al. | 604/366 |
| 4,531,945 | | 7/1985 | Allison | 604/378 |
| 4,535,020 | | 8/1985 | Thomas et al. | 428/131 |
| 4,537,590 | | 8/1985 | Pieniak et al. | 604/379 |
| 4,540,414 | | 9/1985 | Wishman | 604/378 |
| 4,540,454 | | 9/1985 | Pieniak et al. | 156/62.2 |
| 4,559,051 | | 12/1985 | Hanson . | |
| 4,560,372 | | 12/1985 | Pieniak | 604/369 |
| 4,573,988 | | 3/1986 | Pieniak et al. | 604/379 |
| 4,578,066 | | 3/1986 | O'Connor | 604/366 |
| 4,608,292 | | 8/1986 | Lassen | 428/131 |
| 4,610,678 | * | 9/1986 | Weisman et al. | 604/368 |
| 4,623,340 | | 11/1986 | Luceri . | |
| 4,636,207 | * | 1/1987 | Buell | 604/383 |
| 4,636,209 | | 1/1987 | Lassen | 604/378 |
| 4,675,013 | | 6/1987 | Ruffo | 604/366 |
| 4,699,619 | | 10/1987 | Bernardin | 604/378 |
| 4,704,112 | | 11/1987 | Suzuki et al. | 604/378 |
| 4,798,603 | * | 1/1989 | Meyer et al. | 604/378 |
| 4,834,738 | * | 5/1989 | Kielpikavski et al. | 604/385.2 |
| 4,861,652 | * | 8/1989 | Lippert et al. | 604/385.1 |
| 4,883,480 | | 11/1989 | Huffman et al. | 604/385.1 |
| 4,887,002 | * | 12/1989 | Oleary | 604/385.1 |
| 4,935,021 | * | 6/1990 | Huffman et al. | 604/385.1 |
| 4,936,840 | * | 6/1990 | Proxmine | 604/385.2 |
| 4,938,753 | * | 7/1990 | Van Gompel et al. | 604/385.2 |
| 5,069,678 | * | 12/1991 | Yamamoto et al. | 604/358 |
| 5,098,423 | * | 3/1992 | Pieniak et al. | 604/385.1 |
| 5,188,626 | * | 2/1993 | Toyoda e tal. | 604/358 |

\* cited by examiner

DISPOSABLE DIAPER HAVING A HUMIDITY TRANSFER REGION, BREATHABLE ZONE PANEL AND SEPARATION LAYER

CROSS-REFERENCE TO RELATED APPLICATIONS

This is a continuation of application Ser. No. 07/573,861 filed on Aug. 30, 1990, and now abandoned, which is a continuation-in-part of U.S. patent application Ser. No. 07/416,897 filed Oct. 4, 1989 and now abandoned.

FIELD OF THE INVENTION

The present invention relates to an absorbent garment article for absorbing body fluids and exudates, such as urine. More particularly, the present invention relates to absorbent garments, such as disposable diapers and adult incontinence garments, which are configured to absorb body exudates while also helping to provide reduced skin hydration.

BACKGROUND OF THE INVENTION

Breathable polymer films have been employed as outer covers for absorbent garments, such as disposable diapers. The breathable films are typically constructed with micropores to provide desired levels of liquid impermeability and vapor permeability. Other disposable diaper designs have been arranged to provide some level of breathability at the leg cuff regions of the diaper. For example, see U.S. Pat. No. 4,636,207 issued Jan. 13, 1987 to K. Buell.

Diapers and plastic pant overgarments for covering diapers have employed perforated regions to help ventilate the garment. For example, see U.S. Pat. No. 3,081,772 issued Mar. 19, 1963 to H. Brooks et al. and U.S. Pat. No. 2,544,069 issued Mar. 6, 1951 to H. Cutler.

U.S. Pat. No. 4,341,216 issued Jul. 27, 1982 to M. Obenour describes a disposable diaper provided with a two-element breathable backsheet. The two elements are a vapor pervious, relatively liquid impervious outer sheet, and a liquid impervious inner panel.

Other disposable garment designs have employed additional layers of material under the bodyside liner. For example, European Patent Application No. EP 0 165 807 A1 of T. Osborn III published Dec. 27, 1985 describes a sanitary napkin which includes an apertured topsheet and a resilient, reservoir layer underlying the topsheet. The absorbent structure can also include a wicking layer between the apertured topsheet and the resilient layer, an absorbent core underlying the resilient layer, and a moisture barrier located against the outermost side of the absorbent core.

Various types of diaper structures have employed hydrophilic wicking layers to conduct fluid within an absorbent structure. For example, see U.S. Pat. No. 4,388,371 issued Jul. 6, 1982 to F. Dawn et al.; U.S. Pat. No. 4,259,958 issued Apr. 7, 1981 to R. Goodbar; and UK Patent Application No. GB 2 170 108 A of L. Bowman et al. published Jul. 30, 1986.

Still other diaper configurations have employed embossed layers configured to provide raised regions that separate the user from the absorbent pad. For example, see U.S. Pat. No. 4,324,247 issued Apr. 13, 1986 to M. Aziz; U.S. Pat. No. 4,041,951 issued Aug. 16, 1977 to L. Sanford; U.S. Pat. No. 3,945,386 issued Mar. 23, 1976 to E. Anczurowski et al.; and U.S. Pat. No. 4,413,032 issued Nov. 1, 1983 to L. Hartmann et al.

Disposable absorbent articles have also employed an isolating layer between a topsheet layer and an absorbent layer. For example, UK Patent Application No. 2 193 625 A of M. Suzuki et al. published Feb. 17, 1988 includes an isolating layer composed of polyester fibers and having a selected compressive elastic recovery rate under wet conditions. U.S. Pat. No. 4,480,000 issued Oct. 30, 1984 to I. Watanabe et al. describes an absorbent article which includes a web comprised of polyester fiber which is placed on top of an absorbent core layer. The absorbent article is described as being able to absorb fluid at an enhanced rate and to have a feeling of dryness even after such absorption.

U.S. Pat. No. 3,987,792 issued Oct. 26, 1976 to J. Hernandez et al. describes a disposable diaper comprising a water-pervious layer, a spongy, resilient and compressible hydrophobic fibrous layer, an absorbent core, and a water-impervious layer. The hydrophobic fibrous layer is pervious to fluids in the uncompressed condition, but is impervious to fluids when compressed. The description indicates that when compressed, the hydrophobic fibers intermesh to form a seal or barrier.

Conventional absorbent articles, such as those described above, have not been completely satisfactory. For example, articles which employ a microporous outercover can exhibit a cold and clammy feeling when the garment is wetted and moisture is evaporating through the microporous film. The articles which employ perforated films can exhibit excessive leakage of liquids from the article, and can excessively soil the wearer's outergarments. In addition, when the absorbent material of the article becomes loaded with liquid, the wet absorbent can block the escape of moisture from the wearer's skin. Other absorbent garment designs which include additional layers between the bodyside liner layer and the absorbent core layer have not been able to sufficiently reduce the hydration of the wearer's skin. As a result, the wearer's skin has remained susceptible to abrasion and irritation.

BRIEF DESCRIPTION OF THE INVENTION

The present invention provides an absorbent article, which generally delimits a front waistband section, a rear waistband section and an intermediate section which interconnects said front and rear waistband sections. The article comprises a substantially vapor impermeable backsheet layer, a liquid permeable topsheet layer positioned in facing relation with said backsheet layer, and an absorbent body for storing absorbed liquid. The absorbent body is located between the backsheet layer and topsheet layer and includes an absorbent material which provides for a level of moisture retention therein. The absorbent body has a humidity transfer zone portion, and the humidity transfer zone portion can include a substantially hydrophobic, nonwettable fibrous material. The fibrous material can have a basis weight within the range of about 5–300 gsm and can have a density of not more than about 0.1 gm/cc. The nonwettable fibrous material is configured to limit a presence and wicking therein of liquid and to limit an occluding of said nonwettable fibrous material by liquid. The humidity transfer zone portion can thereby exhibiting a relatively lower level of moisture retention as compared to other areas of said absorbent body where said liquid is normally stored. A vapor permeable panel is substantially liquid impermeable, and is connected to said backsheet layer in at least one of said waistband sections. The vapor permeable panel is arranged in an operable adjacent registry with at least a portion of said nonwettable fibrous material of said humidity transfer zone portion to extend at least partially thereover. The connection of said vapor permeable panel to said backsheet layer and the registry of said vapor permeable panel with the humidity transfer zone portion is arranged to allow movement of air into said nonwettable fibrous material through said vapor permeable panel.

In another aspect of the present invention, the absorbent article generally delimits a front waistband section, a rear waistband section and an intermediate section which interconnects the front and rear waistband sections. The article comprises a substantially fluid impermeable backsheet layer, a liquid permeable topsheet layer positioned in facing relation with the backsheet layer, and an absorbent body located between the backsheet layer and topsheet layer. Spacing means, such as one or more liquid permeable separation layers, are located between the topsheet layer and the absorbent body, and are configured to readily allow fluid transfer between the topsheet layer and the absorbent body. The separation layers are composed of a substantially hydrophobic material and have a total bulk caliper of at least about 0.04 cm (measured at a pressure of 0.0207 kPa). A vapor permeable panel is connected to the backsheet layer at a waistband section of the article, and is arranged in an overlying registry with at least a portion of the absorbent body.

The absorbent article of the invention can advantageously provide improved separation between the wearer's skin and the absorbent body. In addition, the absorbent article can provide a more effective dissipation of water vapor away from the wearer's skin and out from the interior of the absorbent article. As a result, the article of the invention can advantageously provide reduced wetness of the wearer's skin (lower skin hydration), and reduced susceptibility to skin abrasion and irritation. The occlusive, humidifying effects of the wet absorbent body can be reduced more effectively, and greater comfort can be provided for the wearer. In addition, the distinctive configuration of the invention can advantageously reduce the cool damp feeling at the outer surface of the article, which can typically occur with the use of backsheet layers composed of breathable films.

BRIEF DESCRIPTION OF THE DRAWINGS

The invention will be more fully understood and further advantages will become apparent when reference is made to the following detailed description of the invention and the accompanying drawings, in which.

DETAILED DESCRIPTION OF THE INVENTION

The following detailed description will be made in the context of a disposable diaper article. It is readily apparent, however, that the absorbent structure of the present invention would also be suitable for other absorbent articles, such as feminine care pads, incontinence garments, and the like.

Figure 1:
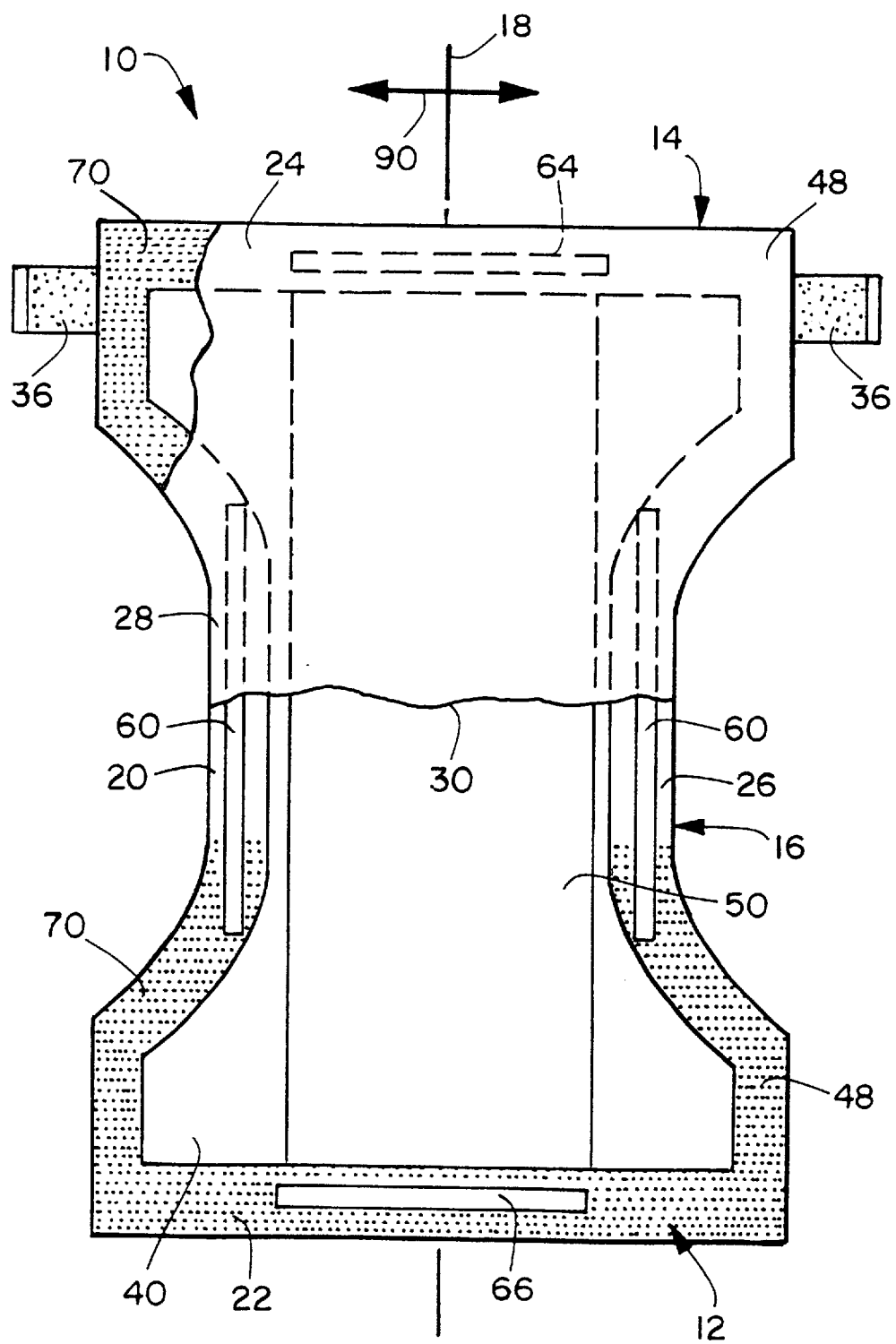
FIG. 1 representatively shows a partially cut away, top plan view of an absorbent article of the invention.
Figure 1A:
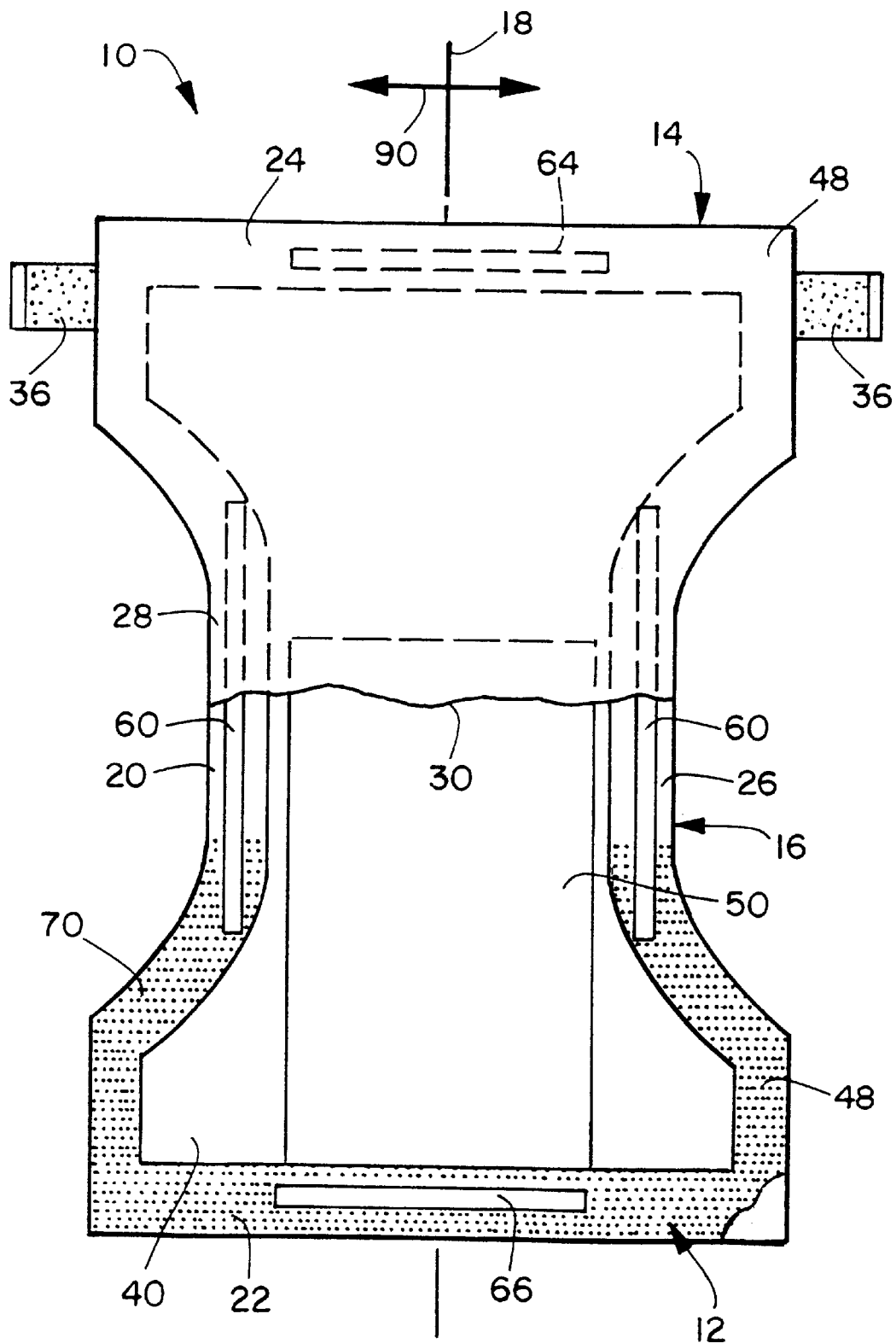
FIG. 1A representatively shows a partially cut away, top plan view of an absorbent article having at least one separation layer limited to a front section of the article, and a composite vapor permeable panel.
Figure 1B:
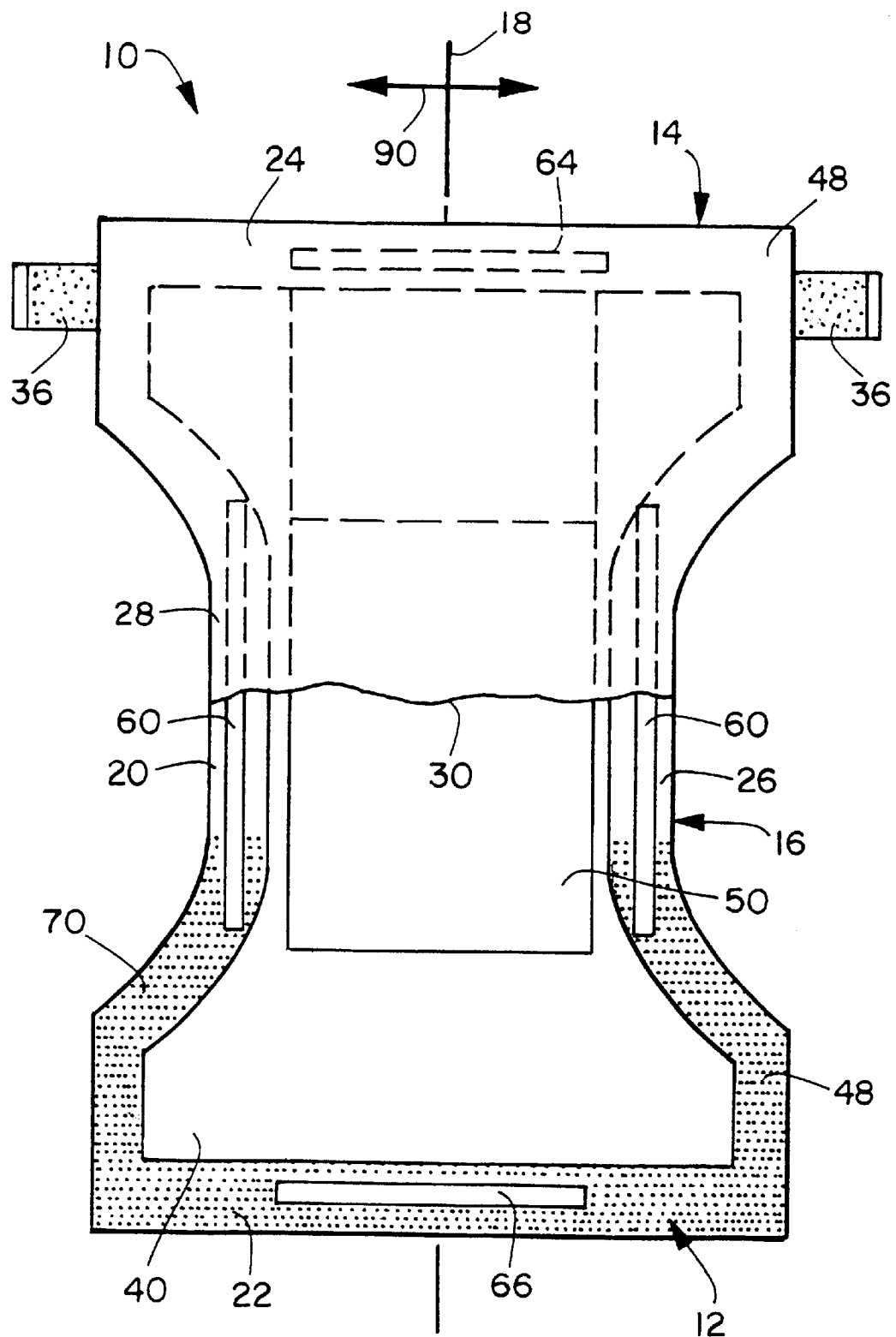
FIG. 1B representatively shows a partially cut away, top plan view of an absorbent article having at least one separation layer limited to a middle section of the article.
Figure 2:
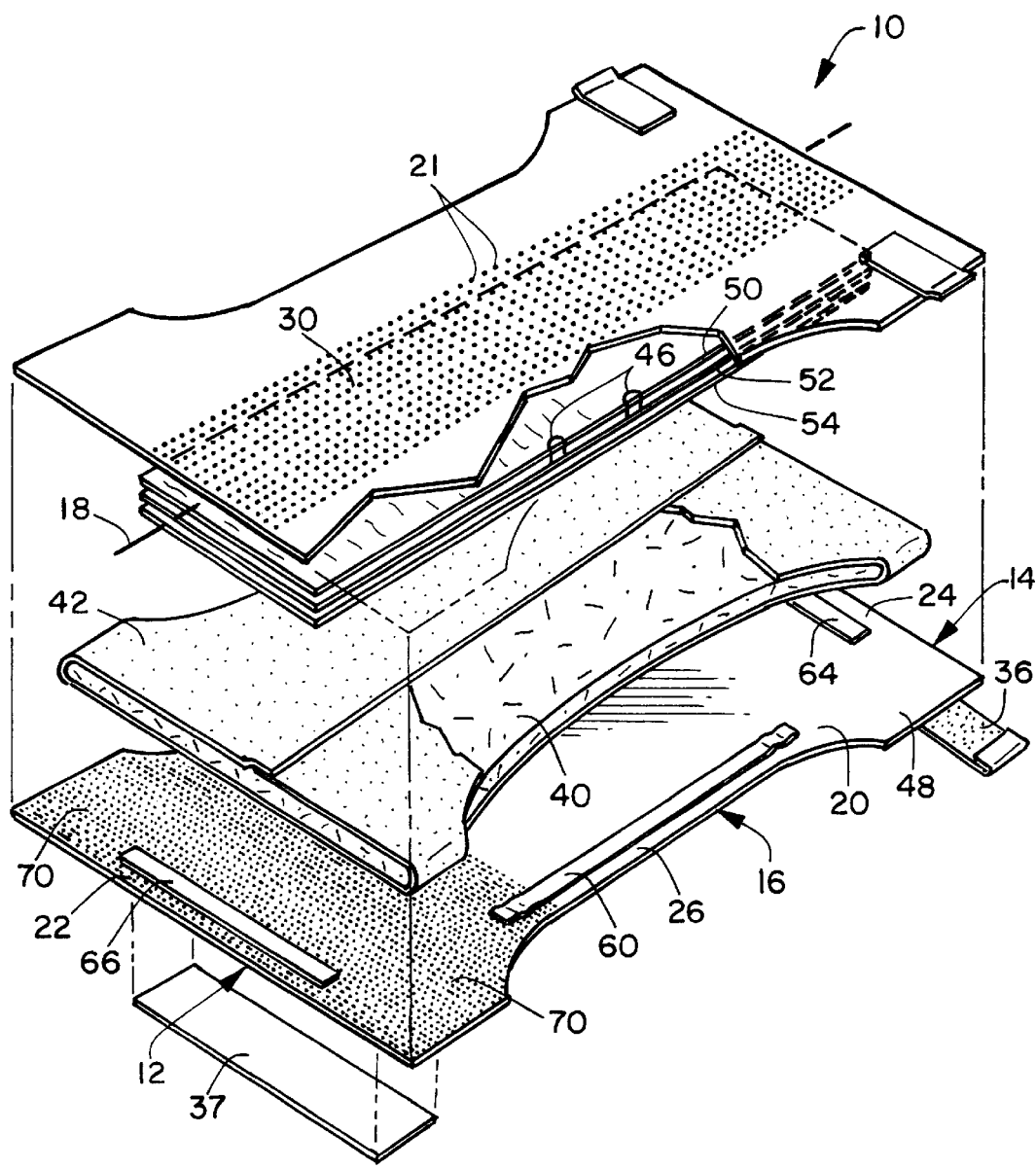
FIG. 2 representatively shows an exploded, partially cut away view of an absorbent article of the invention.
Figure 3:
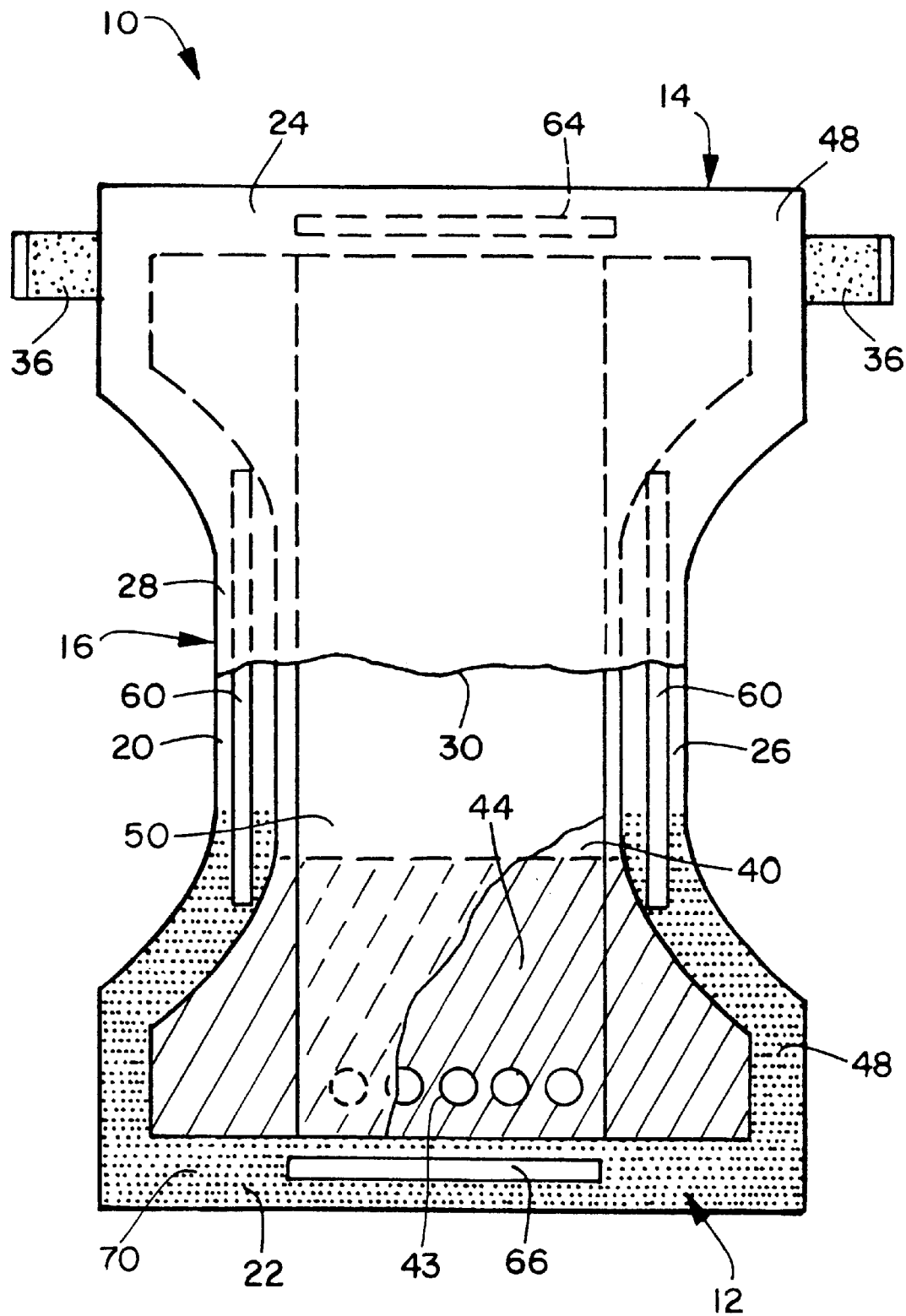
FIG. 3 representatively shows a partially cut away, top plan view of an absorbent article which includes a humidity transfer region.

With reference to FIGS. 1, 2, and 3 an integral absorbent garment article, such as disposable diaper 10, generally delimits a front waistband section 12, a rear waistband section 14, and an intermediate section 16 which interconnects the front and rear waistband sections. The front and rear waistband sections include the general portions of the article which are constructed to extend substantially over the wearer's front and rear abdominal regions, respectively, during use. The intermediate section of the article includes the general portion of the article which is constructed to extend through the wearer's crotch region between the legs. The absorbent article further comprises a substantially fluid impermeable backsheet layer 20, a liquid permeable topsheet layer 30 positioned in facing relation with backsheet layer 20, and an absorbent body 40, such as an absorbent pad, is located between the backsheet layer and topsheet layer. Absorbent body 40 includes a humidity transfer region 44 (FIG. 3) which is configured to exhibit a relatively low moisture retention. A vapor permeable panel, such as breathable panel 70, is substantially liquid impermeable and is operably connected to backsheet layer 20 to extend partially or completely over at least one waistband section of diaper 10. The breathable panel may be an integral portion of the backsheet, or may be a separate component which is assembled to the backsheet. Breathable panel 70 is, for example, composed of a material having a water vapor transmission rate (WVTR) value of at least about 2000 gm/sq. meter/24 hour. In the illustrated embodiment, at least a part of the breathable panel is positioned in a generally adjacent, overlying facing registry with respect to humidity transfer region 44 of absorbent body 40.

In a particular embodiment of the invention, spacing means, such as one or more liquid permeable separation layers 50, may be located between topsheet layer 30 and absorbent body 40 with the separation layers constructed to readily allow fluid transfer between the topsheet layer and absorbent body. Separation layers 50 can be composed of a substantially hydrophobic material and have a total bulk caliper of least about 0.04 cm (measured at a pressure of 0.207 kPa).

Marginal portions of diaper 10, such as marginal sections of backsheet 20, may extend past the terminal edges of absorbent body 40. In the illustrated embodiment, for example, backsheet 20 extends outwardly beyond the terminal marginal edges of absorbent body 40 to form side margins 26 and 28 and end margins 22 and 24 of the garment. Topsheet 30 is generally coextensive with backsheet 20, but may optionally cover an area which is larger or smaller than the area of backsheet 20, as desired.

Diaper 10 may be of various suitable shapes. For example, the diaper may have an overall rectangular shape, T-shape or an approximately hour-glass shape. In the shown embodiment, diaper 10 has a generally I-shape.

The various components of diaper 10 are integrally assembled together employing various types of suitable attachment means, such as adhesive, sonic bonds, thermal bonds or combinations thereof. In the shown embodiment, for example, topsheet 30 and backsheet 20 are assembled to each other and to absorbent body 40 with lines of adhesive, such as a hot melt, pressure-sensitive adhesive. Similarly, other diaper components, such as elastic members 60, 64 and 66 and fastening members 36, may be assembled into the diaper article by employing the above-identified attachment mechanisms.

The illustrated embodiment of diaper 10 includes ear portions 48, which extend laterally along the diaper cross-direction 90 and are positioned at least at the rear waistband section 14 of diaper 10. Ear portions 48 may also be located at front waistband section 12 of the diaper. The ear portions may be integral with backsheet layer 20, or may comprise separate sections, which are composed of the same or different material than backsheet 20 and are suitably assembled and attached to the backsheet layer. Ear sections 48 typically provide extensions of the diaper waistband suitable for completely encircling the waist of the wearer during use.

Fastening means, such as adhesive tapes 36, are employed to secure the diaper on a wearer. Alternatively, other fastening means, such as buttons, pins, snaps, hook-and-loop fasteners, mushroom-andloop fasteners, or the like, may be employed.

To provide improved fit and to help reduce leakage of body exudates from diaper 10, the diaper side margins and end margins may be elasticized with suitable elastic members, such as single or multiple strands of elastic. The elastic strands may be composed of natural or synthetic rubber, and may optionally be heat-shrinkable or heat-elasticizable. Elastic members 60 are constructed to operably gather and shirr side margins 26 and 28 to provide elasticized leg bands which can closely fit around the legs of the wearer to reduce leakage and provide improved comfort and appearance. Similarly, waist elastic members 64 and 66 can be employed to elasticize diaper end margins 22 and 24 to provide elasticized waistbands. The waist elastics are configured to operably gather and shirr the waistband sections to provide a resilient, comfortably close fit around the waist of the wearer. In the Figures, the elastic members are illustrated in their uncontracted, stretched condition for the purpose of clarity.

Backsheet 20 is composed of a substantially fluid impermeable material, which is substantially impermeable to both liquid and gas. In particular, the backsheet is substantially impermeable to at least water and water vapor. An example of a suitable backsheet material is a polymer film composed of polyethylene, polypropylene, or the like. Typically, the polymer film has a thickness within the range of about 0.0007–0.002 inch (0.0018–0.0051 cm). Backsheet 20 may alternatively be composed of a nonwoven fibrous web constructed to provide the required level of fluid impermeability. For example, a nonwoven web composed of spunbonded or meltblown polymer fibers may be selectively treated with a water repellent coating, or laminated with a fluid impermeable, polymer film. In a particular embodiment of the invention, backsheet 20 may comprise a nonwoven web composed of a plurality of randomly deposited hydrophobic thermoplastic meltblown fibers which are sufficiently bonded or otherwise connected to one another to provide a substantially vapor impermeable and substantially liquid impermeable web. The backsheet may also comprise a vapor permeable nonwoven layer which has been partially coated or otherwise configured to provide liquid impermeability in selected areas.

For the purposes of the present invention, a substantially liquid impermeable material is constructed to allow the passage of not more than about 0.05 ml of water within 5 sec after applying a static pressure head of 70 cm of water to the material. Also for the purposes of the present invention, a substantially fluid impermeable or vapor impermeable material is constructed to provide a water vapor transmission rate (WVTR) of not more than about 30 gm/m$^2$/24 hr. A suitable technique for determining the WVTR value is the WVTR Test, which is described in further detail herein below.

Topsheet 30 is typically composed of a liquid permeable, substantially hydrophobic fibrous material, such as a spunbonded web composed of synthetic polymer filaments. Alternatively, topsheet 30 may comprise a meltblown web or a bonded-carded-web composed of synthetic polymer filaments. Suitable synthetic polymers include, for example, polyethylene, polypropylene and polyesters. In a particular aspect of the invention, the polymer filaments have a denier within the range of about 1.5–7 d and preferably have a denier within the range of about 1.5–3 d to provide improved performance. The filaments are arranged to form a layer having a basis weight within the range of about 20–34 gm/m$^2$ (gsm), and preferably are arranged to have a basis weight of about 27 gsm. In addition, the topsheet layer has a bulk thickness within the range of about 0.008–0.017 inches (about 0.0203–0.0432 cm), and preferably has a bulk thickness within the range of about 0.010–0.12 inches (about 0.0254–0.305 cm) for improved effectiveness. The bulk thickness is measured under a restaining pressure of 0.014 psi (0.096 kPa).

Topsheet 30 may optionally be treated with surfactants to adjust its degree of hydrophobicity and wettability. It can also be selectively embossed or apertured with discrete slits or holes 21 (FIG. 2) extending therethrough.

Absorbent body 40 typically includes a pad composed of airlaid, cellulosic fibers commonly referred to as wood pulp fluff. Other natural fibers, such as cotton, may also be employed to form the pad. Conventional absorbent pads can have a density ranging from about 0.05–0.20 grams/cc, and are sufficiently flexible to readily conform to the body of the wearer. Absorbent body 40 may also include a coform material composed of a mixture of cellulosic fibers and synthetic polymer fibers. For example, the coform material may be composed of an airlaid blend of cellulosic fibers and meltblown polyolefin fibers, such as polyethylene and/or polypropylene fibers. Particular examples of the coform material include 2–15 wt % of polyethylene and/or polypropylene fibers. In one aspect of the invention, the fibrous material comprising absorbent body 40 is composed of filaments having a coarseness of about 10–20 mg/100 meters, and preferably having a coarseness within the range of about 10–18 mg/100 meters. The filaments are arranged to form a layer having a basis weight within the range of about 400–1200 gsm, and preferably having a basis weight of about 800 gsm. In addition, the absorbent body material typically has a bulk thickness within the range of about 0.17–0.21 inches (about 0.432–0.533 cm), as measured under a restraining pressure of 0.068 psi (0.47 kPa).

Absorbent body 40 may also include an effective amount of an inorganic or organic high-absorbency (e.g. superabsorbent) material to enhance the absorptive capacity of the absorbent body. For example, absorbent body 40 can contain 5–95 weight percent high-absorbency material, and preferably includes about 10–30 weight percent of the high-absorbency material to provide more efficient performance. Suitable inorganic high-absorbency materials include, for example, absorbent clays and silica gels. Organic high-absorbency materials can include natural materials, such as agar, pectin, guar gum and peat moss, as well as synthetic materials, such as synthetic hydrogel polymers. Such hydrogel polymers include, for example, carboxymethylcellulose, alkali metal salts of polyacrylic acids, polyacrylamides, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers include hydrolyzed acrylonitrile grafted starch, acrylic acid grafted starch, and isobutylene maleic anhydride copolymers, and mixtures thereof. The hydrogel polymers are preferably lightly cross-linked to impart desired levels of water insolubility to the material. Crosslinking may, for example, be by irradiation or by covalent, ionic, Van der Waals, or hydrogen bonding. Suitable materials are available from various commercial vendors, such as Dow Chemical Company, Hoechst Celanese Corporation, Allied-Colloid, and Stockhausen. Typically, the high-absorbency material is capable of absorbing at least about 15 times its weight in water, and preferably is capable of absorbing at least about 25–50 times its weight in water.

The high-absorbency material can be distributed or otherwise incorporated into absorbent body 40 by employing various techniques. For example, the high-absorbency material can be incorporated into a separate carrier sheet which is layered with a body of airlaid cellulosic fibers. Alternatively, the high-absorbency material may be substantially uniformly distributed within the mass of fibers comprising the absorbent body. The material can also be non-uniformly distributed among the fibers to form, for example, a generally continuous gradient with either an increasing or decreasing concentration of high-absorbency material, as determined by observing the concentration moving from the body-side of absorbent body 40 toward the outer-side of the absorbent body. The high-absorbency material may also comprise one or more discrete layers or strips selectively segregated from the fibrous material of absorbent body 40.

The high-absorbency material can itself be configured in various particle shapes. For example, particles of high-absorbency material may be configured in the form of granules, flakes, fibers, or the like.

Optionally, a substantially hydrophilic tissue wrap 42 (FIG. 2) may be employed to help maintain the integrity of the airlaid fibrous structure of absorbent body 40. The tissue wrap sheet is typically placed about the absorbent body over at least the two major facing surfaces thereof, and composed of an absorbent cellulosic material, such as creped wadding or a high wet-strength tissue. In one aspect of the invention, the tissue wrap can be configured to provide a wicking layer which helps to rapidly distribute liquid over the mass of absorbent fibers comprising the absorbent body. In another aspect of the invention, the wrapsheet material on one side of the absorbent fibrous mass may be bonded to the wrapsheet located on the opposite side of the fibrous mass. The bonds are positioned at discrete, separate regions and extend through the thickness of the fibrous mass. Such a configuration effectively shapes the wrapsheet to form a plurality of individual "funnels" or "quilts" which can help to direct liquids into the interior of the fibrous mass and provide a more rapid absorption of the liquid. An effective embodiment may further include a plurality of holes or apertures formed at least partially through the thickness of the fibrous mass. The embodiment is configured such that the bonding of the oppositely positioned layers of wrapsheet material occurs through these holes or apertures. The apertures limit the amount of intervening fibrous material, and allow a more direct bonding between the wrapsheet layers. The bonding can comprise adhesive bonds, sonic bonds, thermal-bonds, or the like.

In particular embodiments of the invention, spacing means, such as at least one liquid permeable, separation layer 50, can be interposed in facing, adjacent relation between topsheet 30 and absorbent body 40. An effective spacing means is configured to be liquid permeable while retaining and holding as little of the liquid as practicable. As a result, the spacing means can maintain a relatively dry region interposed between the wetted absorbent body and topsheet 30. The spacing means can also be advantageously configured to provide a regular or irregular network of void spaces or channels to facilitate the movement of air within the diaper. In the shown embodiment, separation layer 50 is composed of a nonwoven fibrous web composed of natural fibers and/or synthetic polymer fibers. Suitable fibers include, for example, acrylic fibers, nylon fibers and blends thereof. Other suitable polymer fibers may, for example, be composed of a polyolefin, such as polyethylene, polypropylene, polyester or blends thereof. As an example, the web may be a composite of polypropylene fibers and polyethylene fibers. The polymer fibers are typically hydrophobic, but may be treated with a selected amount of surfactant to adjust the wettability thereof. When treated with surfactant, however, the separation layer should still be less hydrophilic than the material comprising absorbent body 40. The presence of an effective amount of the surfactant can advantageously increase the rate of movement of liquid into absorbent body 40 during the initial discharges of liquid into the absorbent article.

Thickness is an important parameter for separation layer 50, and can be measured under both a low constraining pressure (0.207 kPa) and a high constraining pressure (50.37 kPa). A suitable device for performing the high pressure (50.37 kPa) thickness measurement is a Testing Machine, Inc., Model 49-70 Bulk Testing Apparatus with a 1.59 cm diameter platen. The low pressure, 0.03 psi (0.207 kPa), thickness measurement can be performed with thickness measuring apparatus which employs a circular, 7.62 cm (3 inch diameter) platen to exert a pressure of 0.03 psi onto a sample placed on a non-resilient, rigid surface. For example, a suitable instrument for measuring bulk thickness at the low pressure included a STARRETT granite surface plate, which is available from L. F. Starrett Company, located in Aphol, Mass. The instrument further included a movable 7.62 cm diameter platen actuated by a Clipper air valve foot petal assembly, Catalog #3C30A2-S, which is available from Linemaster Switch Corporation, located in Woodstock, Conn. The thickness readout was provided by a Digimatic Indicator manufactured by Mitutoyo Manufacturing Company Limited, Japan, and distributed by MTI Corporation of Paramus, N.J. The indicator has a range between 0.001–2.0 inches.

To provide a desired degree of effectiveness, separation layer 50 has a dry bulk thickness dimension (at 0.207 kPa) of at least about 0.04 cm, and preferably has a dry bulk thickness within the range of about 0.07–0.51 cm. When measured at 50.37 kPa, separation layer 50 has a dry bulk thickness of at least about 0.025 cm, and preferably has a dry bulk thickness within the range of about 0.025–0.1 cm. If separation layer 50 is too thin, it may not provide a sufficient amount of separation and spacing between topsheet 30 and absorbent body 40. Similarly, if the combined bulk thickness of topsheet 30 and separation layer 50 is too thin, there may be insufficient separation and spacing between absorbent body 40 and the skin of the wearer. Accordingly, separation layer 50 and topsheet 30 have a combined bulk thickness (at 0.207 kPa) of at least about 0.078 cm, and preferably have a combined bulk thickness within the range of about 0.1–0.6 cm. When measured at 50.37 kPa, the combined bulk thickness of topsheet 30 and separation layer 50 is at least about 0.039 cm, and preferably is within the range of about 0.039–0.12 cm.

The separation layer can have a basis weight of at least about 25 gsm. In particular aspects of the invention, the basis weight is at least about 34 gsm, and preferably is at least about 55 gsm to provide improved effectiveness. In other aspects of the invention, the basis weight is not more than about 170 gsm, and preferably, is within the range of about 55–170 gsm. To maintain a desired effectiveness of separation layer 50, the separation layer should be capable of sustaining its spacing function even after being wetted by urine or other aqueous liquids discharged from the wearer and after being subjected to the typical pressures exerted by the wearer during use.

In a particular aspect of the invention, the separation layer is configured to maintain a desired level of dryness. In particular, the separation layer material can be constructed to advantageously yield a desorption ratio of at least about 100. The desorption ratio can be determined as follows:

A separation layer sample measuring 2 inch×2 inch in size is weighed and then immersed in a 0.9 percent saline solution for 1 minute. The saline is adjusted with TWEEN 20 to provide a surface tension of approximately 55 dynes/cm. Tween 20, also called polysorbate 20, is a surfactant made by ICI Americas, Inc. of Wilmington, Del., and is composed of a mixture of laurate esters of sorbitol and sorbitol anhydride. The sample is removed from the saline solution, placed on a clip for suspension in a vertical position from a ring stand, and allowed to drip for 1 minute. After this 1 min drip period, the sample and any retained liquid are weighed. The sample is then placed on a desorption pad for 1 hour under a pressure of 3.45 kPa, which is applied over substantially the entire surface of the sample. The sample and any liquid remaining therein are weighed after the one hour desorption period. The desorption pad measures 2 inches×2 inches, and is composed of a woodpulp fluff web having a basis weight of about 800 gsm and containing about 15 wt % of a superabsorbent polyacrylate, hydrogel material.

The desorption ratio is calculated as follows:

Desorption ratio=A/B

Where:
A=weight gain of sample after the saturation/drip process.
B=weight gain of sample after the 1 hour desorption process.

The fibers comprising separation layer 50 are configured to have a denier within the range of about 1.5–15 d, and preferably have a denier within the range of about 1.5–6 d. In addition, separation layer 50 is constructed to have a basis weight of at least about 34 grams per sq. meter (gsm), and preferably has a basis weight within the range of about 55–170 gsm. The separation layer can also have a bulk density (at 0.207 kPa) which is within the range of about 0.03–0.5 g/cc, and preferably is within the range of about 0.07–0.5 g/cc to provide further advantages.

To maintain the desired effectiveness of separation layer 50, the separation layer should be capable of sustaining its above-described spacing function even when wetted by urine or other aqueous liquids discharged from the wearer. Accordingly, the wet compression recovery value of separation layer 50 is at least about 65%. Preferably, the wet compression recovery value is at least about 80%, and more preferably is at least about 85% to provide improved performance.

The compression recovery value is a measure of the "springiness" or resilience of the material, and can be determined by the following procedure. The original thickness ($t_0$) of the separation layer material is first measured under a restraining pressure of 0.1 psi (0.689 kPa). After this measurement, the pressure on the separation layer material is gradually increased to 3 psi (20.7 kPa). The compressive pressure is then gradually reduced until the restraining pressure again reaches 0.1 psi. At this point, the bulk thickness is again measured at the 0.1 psi restraining pressure to obtain a recovery thickness value ($t_R$). The compression recovery value is then determined in accordance with the following formula:

$$\text{Compression recovery value (CRV)} = (t_R/t_0) \times 100\%$$

A suitable instrument for determining the compression recovery value is a Standard Model Compressometer, which is distributed by Frazier Precision Instrument Co. of Gaithersburg, Md. For the purposes of the compression recovery test, the instrument is configured with a one inch diameter foot.

When the above determination is made employing a dry separation layer, one obtains a dry compression recovery value. When the above determination is made employing a separation layer substantially saturated with distilled water, one obtains a wet compression recovery value. In a particular aspect of the invention, the separation layer has a dry CRV of at least about 65% and a wet CRV of at least about 65%. A preferred embodiment of the invention has a dry CRV and a wet CRV which both are at least about 80% to provide improved performance.

In a further aspect of the invention, the absorbent garment includes a plurality of two or more separation layers positioned in facing adjacent relationship and located between topsheet 30 and absorbent body 40. In particular, 2–5 individual separation layers may be located between the topsheet and the absorbent body. FIG. 2, for example, representatively shows an embodiment having three separation layers 50, 52, 54. It has been found that a plurality of separation layers may advantageously provide improved effectiveness with respect to reducing the amount of moisture at the wearer's skin. While not intending to be bound by any particular theory, it appears that the interstitial spaces between the individual separation layers can help isolate the wearer's skin away from the wet absorbent and help improve the movement of water vapor away from the wetted skin. In a particular embodiment of the invention, the separation layers can help facilitate the circulation of drier ambient air into the diaper through breathable panel 70.

The individual separation layers are distinct and separate from each other, but may be joined at selected, limited locations to maintain the integrity of the assembly. For example, the individual separation layers 50, 52, 54 may be spotbonded to each other at limited, discrete locations 46 arranged in a selected pattern. The multiple separation layers have a combined, total bulk thickness (measured dry at 0.207 kPa) of at least about 0.04 centimeters, and preferably have a combined total bulk thickness within the range of about 0.07–0.51 cm. When measured at 50.37 kPa, the combined separation layers have a total dry bulk thickness of at least about 0.025 cm, and preferably have a total dry bulk thickness within the range of about 0.025–0.1 cm. In addition, the total bulk thickness (at 0.207 kPa) of topsheet 30 in combination with the multiple separation layers is at least about 0.078 cm, and preferably the combined total bulk thickness is within the range of about 0.1–0.6 cm. When measured at 50.37 kPa, the combined bulk thickness of topsheet 30 and the multiple separation layers is at least about 0.039 cm, and preferably the combined bulk hickness is within the range of about 0.039–0.12 cm. The multiple separation layers, in combination together, should exhibit a composite desorption ratio of at least about 100 when tested by the above-described desorption procedure. The multiple separation layers can have a combined effective basis weight of at least about 25 gsm. In particular aspects of the invention, the combined effective basis weight is at least about 34 gsm, and preferably is at least about 55 gsm. In other aspects of the invention, the combined effective basis weight is not more than about 170 gsm, and preferably, is within the range of about 55–170 gsm. The multiple separation layers can further have an effective bulk density (measured at 0.207 kPa) which is within the range of about 0.03–0.5 grams/cc, and preferably is within the range of about 0.07–0.5 grams/cc.

The separation layers may extend completely or partially over the adjacent surface area of absorbent body 40. Preferably, the separation layers are positioned over the intermediate section 16 of disposable diaper 10, and are substantially centered side-to-side with respect to the longitudinal centerline 18 of the disposable diaper. The separation layers extend over about 35–100% of the total longitudinal length of diaper 10, and extend over about 50–100% of the width of the diaper, as measured at the narrowest portion of the diaper intermediate section 16. In the illustrated embodiment of the invention, the separation layers extend over a cross-directional width of about 12.7 cm and extend over a longitudinal length of about 38.1 cm.

In a particular embodiment of the invention, the separation layer or layers can be limited to a front two-thirds section of the diaper. In yet another embodiment of the invention, the separation layers can be limited to a medial 35–60% portion of the longitudinal length of diaper 10, and may be offset lengthwise towards the front waistband section of the diaper.

In the embodiment of the invention employing multiple separation layers, the individual separation layers may extend over the same or different areas. For example, separation layer 50 may cover a larger surface area than separation layer 52, and separation layer 52 may cover a larger surface area than separation 54. The individual separation layers may also be composed of different materials. For example, each of the separation layers could be composed of a different polymer fiber, or could be composed of the same polymer fiber but have different basis weights.

The multiple separation layers have a composite compression recovery value (CRV) when dry of at least about 65% and preferably have a composite, dry CRV of at least about 80%. In addition, the multiple separation layers have a composite wet CRV of at least about 65%, and preferably have a combined, wet CRV of at least about 80% to provide improved effectiveness.

While not intending to be bound by any particular theory, it is believed that the presence of the separation layer (or layers) can advantageously provide a more effective spacing of the wearer's skin away from the wet absorbent pad and can provide improved circulation of moist air and water vapor away from the region immediately adjacent the wearer's skin. In conventional designs, the closer proximity of the skin to the wetted absorbent body can produce an occlusive effect which helps trap and hold the moist, humid air against the skin. The incorporation of an effective separation layer, however, can help provide more open spaces and irregular channels which better allow the humid air to move away from the wetted region of the absorbent body and allow drier air; e.g., from the waistband sections of the article; to circulate into the wetted region. The drier air can then help reduce any excessive hydration of the skin.

A breathable panel 70, which is substantially liquid impermeable but vapor permeable, can be located in at least one waistband section of diaper 10 to provide distinctive advantages and improvements. Particular embodiments of the invention can optionally incorporate the breathable panel in combination with the separation layer (or layers) discussed above. In the shown embodiment, the breathable panel is constructed to extend from backsheet 20 at the diaper front waistband section 12. Alternatively, a breathable panel may be located at the diaper rear waistband section 14, or breathable panels 70 may be located at both the front and rear waistband sections of diaper 10. Breathable panel 70 is substantially liquid impermeable, but is significantly more vapor permeable than backsheet layer 20. In particular, the breathable panel may comprise a material having a water vapor transmission rate (WVTR) value of at least about 2,000 gm/sq. meter/24 hrs. Preferably, the breathable panel has a WVTR of at least about 4,000 gm/sq. meter/24 hrs, and more preferably has a WVTR of at least about 5,000 gm/sq. meter/24 hrs to provide improved performance. In addition, breathable panel 70 has an effective breathable area of at least about 22 $cm^2$. In particular aspects of the invention, the effective breathable area is at least about 45 $cm^2$, and preferably the effective breathable area is within the range of about 45–400 $cm^2$ to provide further advantages.

The effectiveness of the breathable panel can be advantageously improved by positioning at least a section of the breathable panel in an adjacent, overlying relation with respect to a selected waistband portion of absorbent body 40. It has been found that such an overlying registry can more effectively reduce skin hydration, and can better cooperate with any separation layer or layers to help remove humidity from the area adjacent the wearer's skin and circulate drier air to the skin area covered by the wetted absorbent body. The configuration of the present invention distinctively provides a substantially fluid impermeable backsheet in the intermediate, crotch section of the diaper and limits the breathable panel sections to the waistband sections of the diaper, which are relatively remote from the target regions of the absorbent body that typically receive direct wetting from the wearer. As a result, lesser amounts of the relatively expensive breathable panel material are needed. It is noted that conventional diaper designs have employed outer covers totally composed of a breathable but liquid impermeable material, such as microporous polymer film. Such designs have been configured to evaporate water from a wetted absorbent pad through the breathable outer cover and thereby dry the pad and regenerate its absorbent capacity. The diaper designs, however have been expensive to manufacture, and can exhibit a cold, clammy feeling on the diaper due to the moisture evaporating from the surface of the outer cover.

In contrast to ordinary designs, it has been discovered that the objective of reducing skin hydration can be better accomplished by restricting the breathable portion of the outer cover to overlie the absorbent body at the more remote waistband sections of the diaper. It has been found that directing air movement through the dry sections of the absorbent can be more effective with respect to reducing skin hydration. With the article of the present invention, moisture from the wearer's skin can still readily move out of the diaper and dry replacement air can more effectively move into the diaper to the region adjacent the skin. The replacement air can be substantially precluded from moving into the diaper along a path through the wetted absorbent. As a result, the replacement air is less liable to become excessively humidified prior to reaching the wearer's skin.

It has been found that further advantages can be obtained by an arrangement comprising a combination of breathable panel 70 with one or more separation layers. One advantage, for example, is that with such an arrangement, breathable panel 70 can be effective even when its vapor permeable area is reduced to an area which is only at least about 0.785 in$^2$ (about 5 cm$^2$). Accordingly, the vapor permeable area of panel 70 can be within the range of about 5–400 cm$^2$. As a result, the cost of an operable absorbent article may be further reduced by using even less of the liquid impermeable but vapor permeable material.

If breathable panel 70 is partially covered or occluded by another, substantially vapor impermeable component of diaper 10, the areal extent of breathable panel 70 should be appropriately increased to compensate for the breathable area obscured by the occluding component. For example, when adhesive tapes are used as fastening means for the diaper, a tape landing zone composed of a plastic film may be attached to the outward surface of breathable panel 70 to provide a refastenable adhesive tape system. While the plastic film may be vapor permeable or vapor impermeable, the securement of tape landing zone 37 over the breathable panel could excessively occlude a portion of the breathable panel and might require an increase of the breathable surface area at other locations of panel 70. Similarly, where diaper 10 includes a hook-and-loop fastening system, such as a VELCRO fastener, the loop material may be located over an outwardly facing surface of breathable panel 70. While the loop material may itself be vapor permeable, the adhesive or other bonding system employed to secure the loop material over breathable panel 70 may be substantially vapor impermeable. To reduce the amount of occlusion of panel 70, a discontinuous, open pattern of the adhesive or other bonding mechanism may be employed to secure the loop material onto the breathable panel. For example, where an adhesive is employed, an open pattern of sprayed droplets or sprayed filaments may be employed to secure the component onto the breathable panel.

Breathable panel 70 may be composed of a micro-porous polymer film, such as Grade PMP-1 film, manufactured by Mitsui Toatsu Chemical, Inc., Tokyo, Japan. Alternatively, breathable panel 70 may be composed of a nonwoven fibrous material, such as a spunbonded or meltblown web composed of synthetic polymer fibers.

In a particular aspect of the invention, breathable panel 70 is composed of a calendered, composite, fibrous web, which includes a barrier layer comprising fine fibers and a reinforcing layer comprising coarse fibers. The barrier layer and reinforcing layer are securely bonded together by fusing or adhering the reinforcing fibers into the barrier fibers, and the reinforcing layer is configured to form the outwardly facing surface of the composite web.

The reinforcing layer of the composite can be a web of hydrophobic fiber material arranged to provide a web basis weight within the range of about 10–35 grams per square meter. The reinforcing layer has a grab tensile strength within the range of about 1500–10,000 grams/inch, and is bonded with a spot bonding pattern which covers between about 3–20% of the surface area of the reinforcing layer. The barrier layer of the composite is a web of hydrophobic fiber material arranged to provide a basis weight within the range of about 10–50 gsm. The barrier layer is composed of a plurality of randomly deposited, essentially continuous, hydrophobic, thermoplastic fibers which are partially bonded to one another. Such a web may be produced by meltblowing a web composed of thermoplastic polymer micro-fibers having an average cross-sectional diameter of about 3.0 micrometers or less.

The barrier layer and reinforcing layer are securely bonded to each other with a discontinuous bond pattern composed of thermal bonds, sonic bonds, thermal or pressure activated adhesive resin, or the like. This interlayer bonding pattern covers an area within the range of about 3–20% of the surface area of the composite web. A suitable composite web exhibits a porosity value within the range of about 3–15.25 cubic meters/minute/square meter, and can support a hydrohead of at least 70 cm of water for a period of 5 sec with a visible leakage therethrough of no more than a drop (0.05 cc) of water.

As representatively shown in FIG. 2, breathable panel 70 can optionally be a separate component which connects to and extends laterally and longitudinally across the front waistband section 12 of diaper 10. Breathable panel 70 may extend across the complete cross-directional width of diaper 10, as illustrated in the shown embodiment. Alternatively, breathable panel 70 may extend partially across the diaper cross-directional width. For example, the breathable panel may comprise a sheet component which spans across a notch or recess, or a "window"-type opening formed into the layer of backsheet material. To provide the desired amount of breathable surface area, panel 70 can have a longitudinal dimension within the range of about 2–18 centimeters. In a particular aspect of the invention, breathable panel 70 extends over at least about 10%, and preferably over at least about 15%, of the longitudinal length of the absorbent body to provide improved performance. In another aspect of the invention, the breathable panel can be constructed to extend over not more than about 40%, and preferably over not more than about 30% of the length of the absorbent body to provide further advantages. The shown embodiment of panel 70 extends over about 20% of the longitudinal length of absorbent body 40, beginning at the terminal, front waistband edge of the absorbent body. While the illustrated embodiment shows a breathable panel which extends completely to the terminal, waistband edge of the diaper article, it should be readily appreciated that the extent of panel 70 along the diaper longitudinal direction may optionally stop short of the terminal, waistband edge.

Referring to FIG. 3, the effectiveness of the present invention can be improved by constructing absorbent body 40 to include a humidity transfer region 44 which is positioned in an operable, adjacent registration with breathable panel 70. The humidity transfer region has a relatively low moisture retention, as compared to the other sections of the absorbent body where liquid is normally held and stored. For example, the humidity transfer region may comprise a substantially hydrophobic, nonwettable fibrous material, such as layer or other suitable mass of polyester fibers.

In a particular aspect of the invention, the humidity transfer region has a Moisture Retention Index of not more than about 40 gm. Preferably, the humidity transfer region has a Moisture Retention Index of not more than about 30 gm, and more preferably, has a Moisture Retention Index of not more than about 20 gm. The low Moisture Retention Index of the humidity transfer region can advantageously help limit the occluding effect produced by presence of held liquids. As a result, water vapor can more readily escape from the spaces adjacent the wearer's skin.

The humidity transfer region can also be advantageously configured to have a Wicking Index of not more than about 0.2 gm. Preferably, the humidity transfer region has a Wicking Index of not more than about 0.1 gm and more preferably, has a Wicking Index of not more than about 0.05 gm to provide improved effectiveness. The relatively low Wicking Index of the humidity transfer region helps to limit the presence of liquid which could inhibit the movement of water vapor away from the wearer's skin.

In another aspect of the invention, the humidity transfer region can be composed of a composite structure. For example, the humidity transfer region can comprise a multi-layer composite composed of one or more cellulosic tissue layers, nonwoven fibrous polymer web layers, woven fabric layers or combinations thereof. Each of the layers may be wettable or nonwettable, as desired.

The humidity transfer region, in one embodiment of the invention, has a density of not more than about 0.1 gm/cc, and in another embodiment of the invention, the density of the humidity transfer region is not less than about 0.001 gm/cc. Preferably, the humidity transfer region has a density within the range of about 0.001–0.05 gm/cc to provide improved effectiveness. In a further aspect of the invention, the humidity transfer region can have an average basis weight of not more than about 550 gsm, and preferably has an average basis weight within the range of about 5–300 gsm for improved performance. To further assist in its effectiveness, the humidity transfer zone can be configured with a bulk thickness of not less than about 0.02 in (about 0.051 cm), when measured dry at 0.2 psi (1.38 KPa). Preferably, the humidity transfer region has a bulk thickness of not less than about 0.08 in (about 0.203 cm), and more preferably, has a bulk thickness of not less than about 0.10 in (about 0.254 cm) to better assist in reducing skin hydration. A particular aspect of the invention comprises a configuration wherein the humidity transfer region has a Frazier air porosity value of at least about 15.25 $m^3/min/m^2$, and another aspect of the invention comprises an arrangement wherein the humidity transfer region has a Frazier air porosity value within the range of about 15.25–30 $m^3/min/m^2$.

Figure 7:
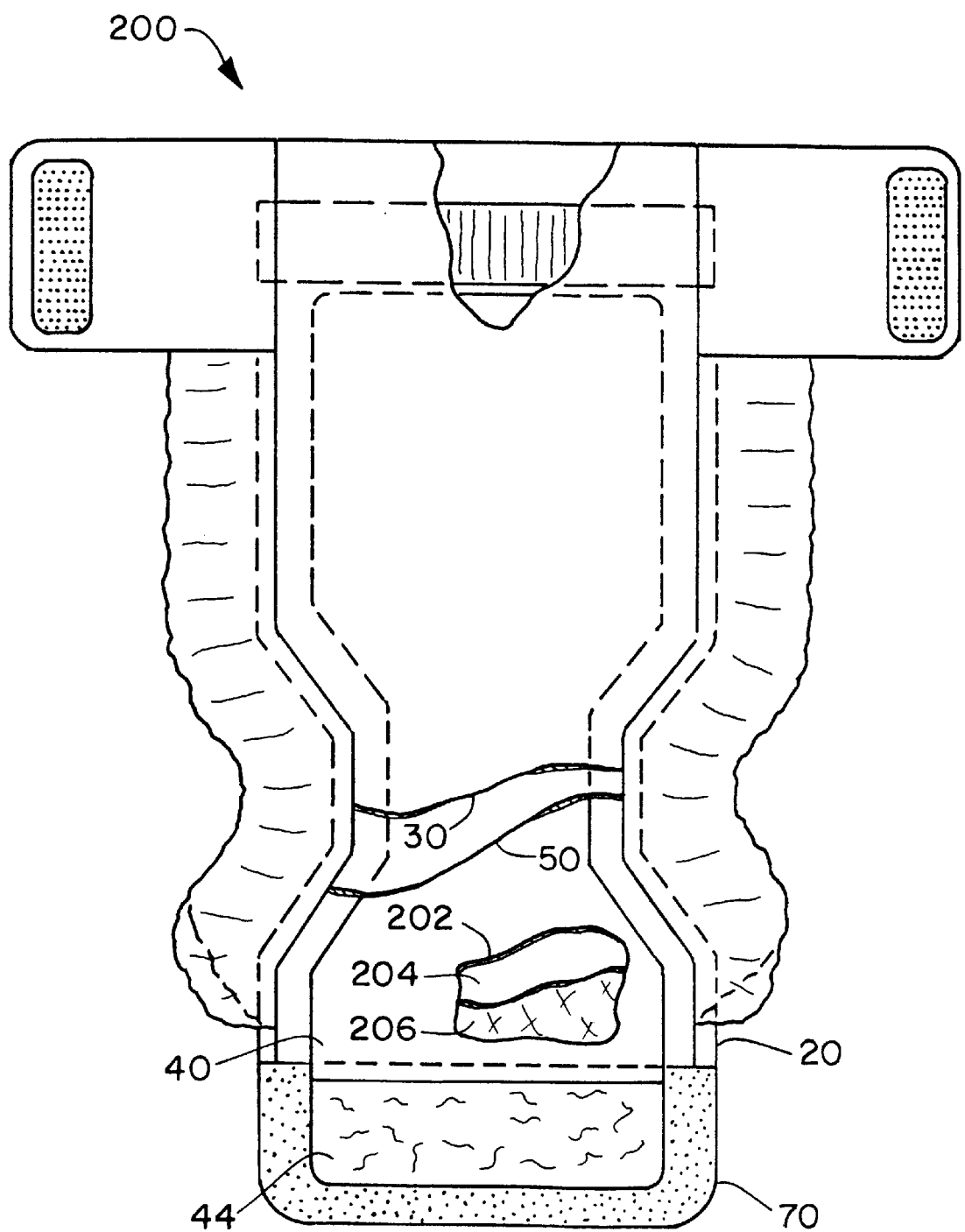
FIG. 7 representatively shows a partially sectioned view of disposable diaper having an absorbent composite with a humidity transfer region.
Figure 8:
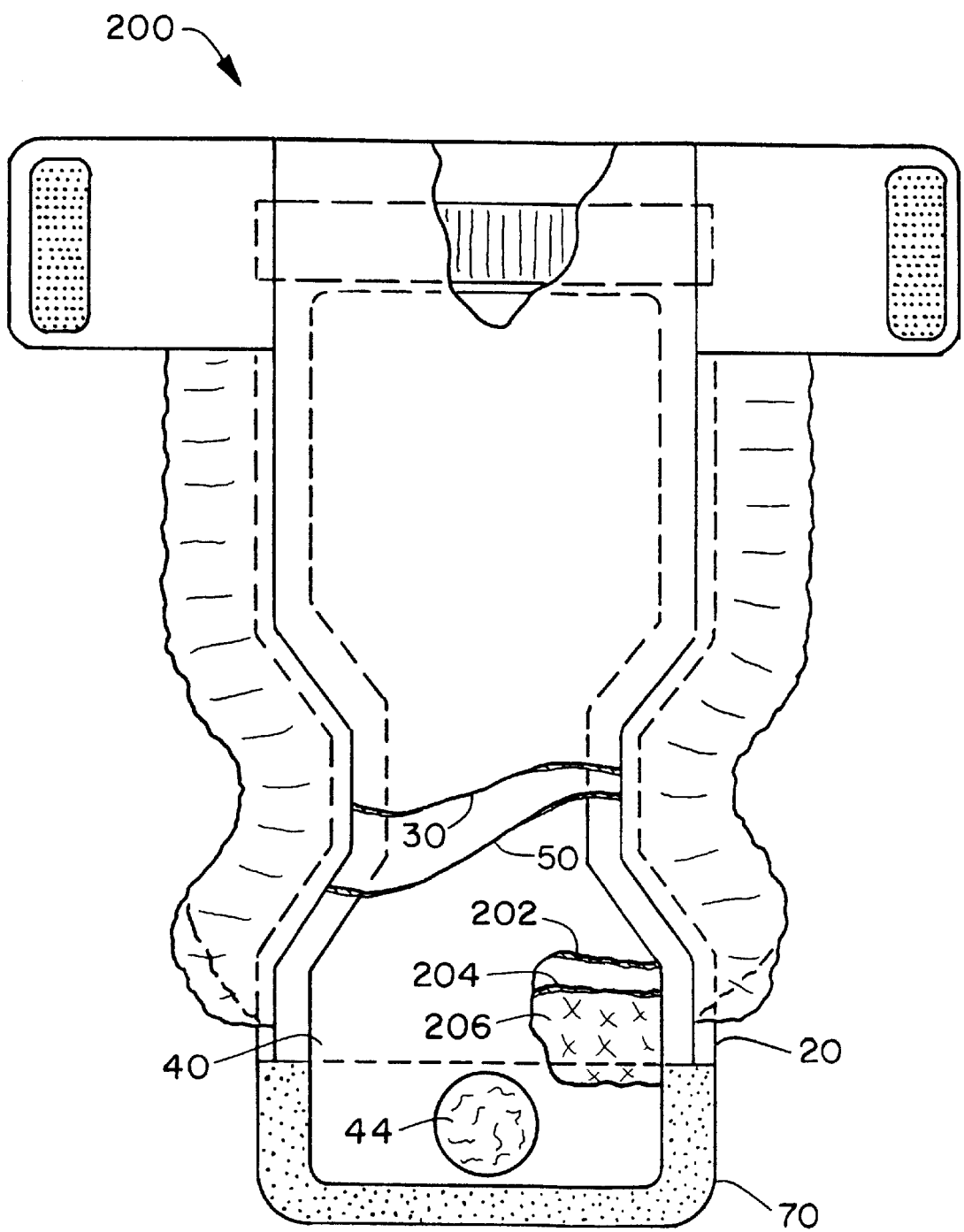
FIG. 8 representatively shows a partially sectioned view of an article having an absorbent body where the humidity transfer region is in the shape of a circle.
Figure 8A:
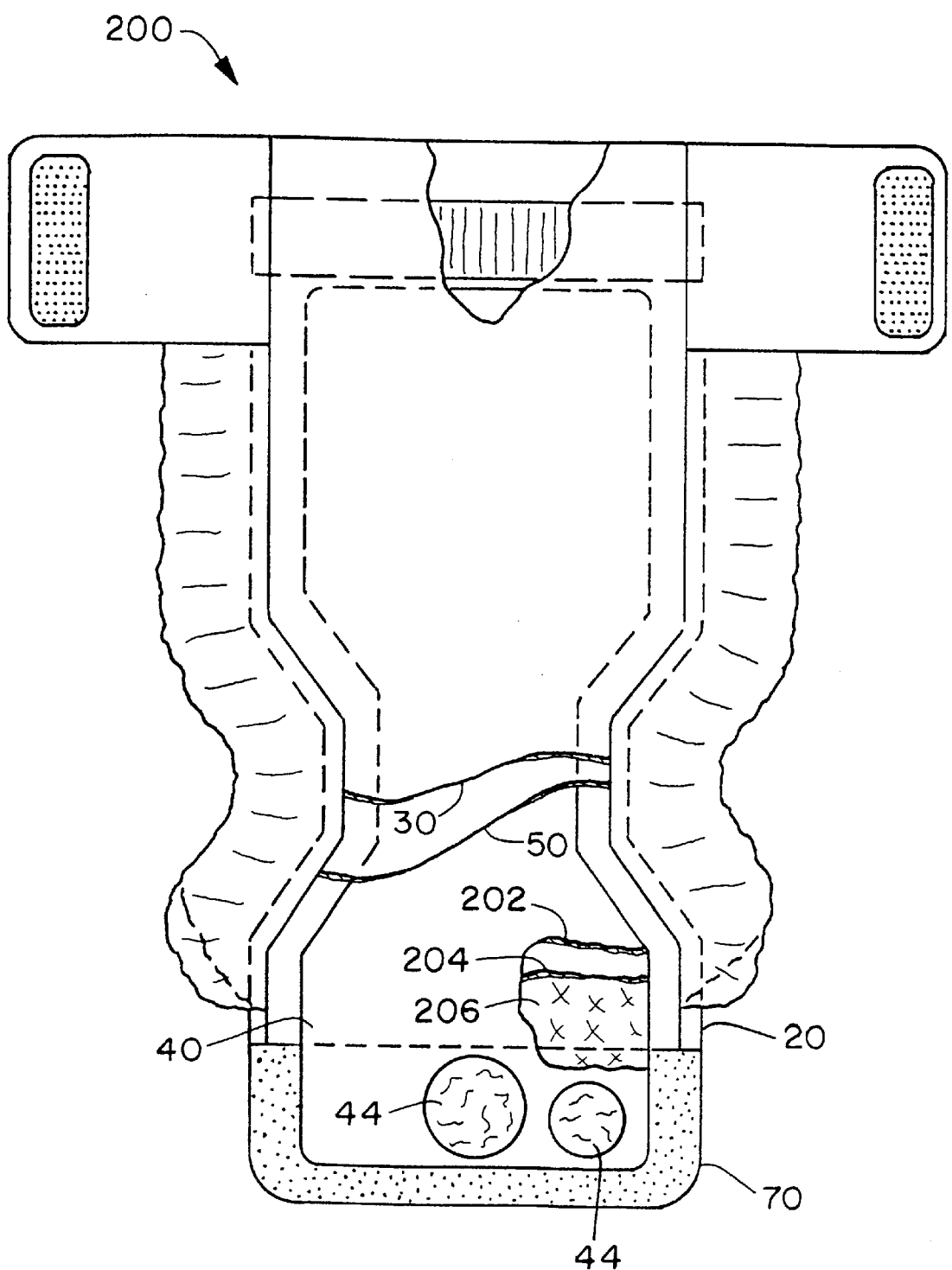
FIG. 8A representatively shows a partially sectioned view of an absorbent body having a plurality of apertures with nonwettable fibrous material.
Figure 10:
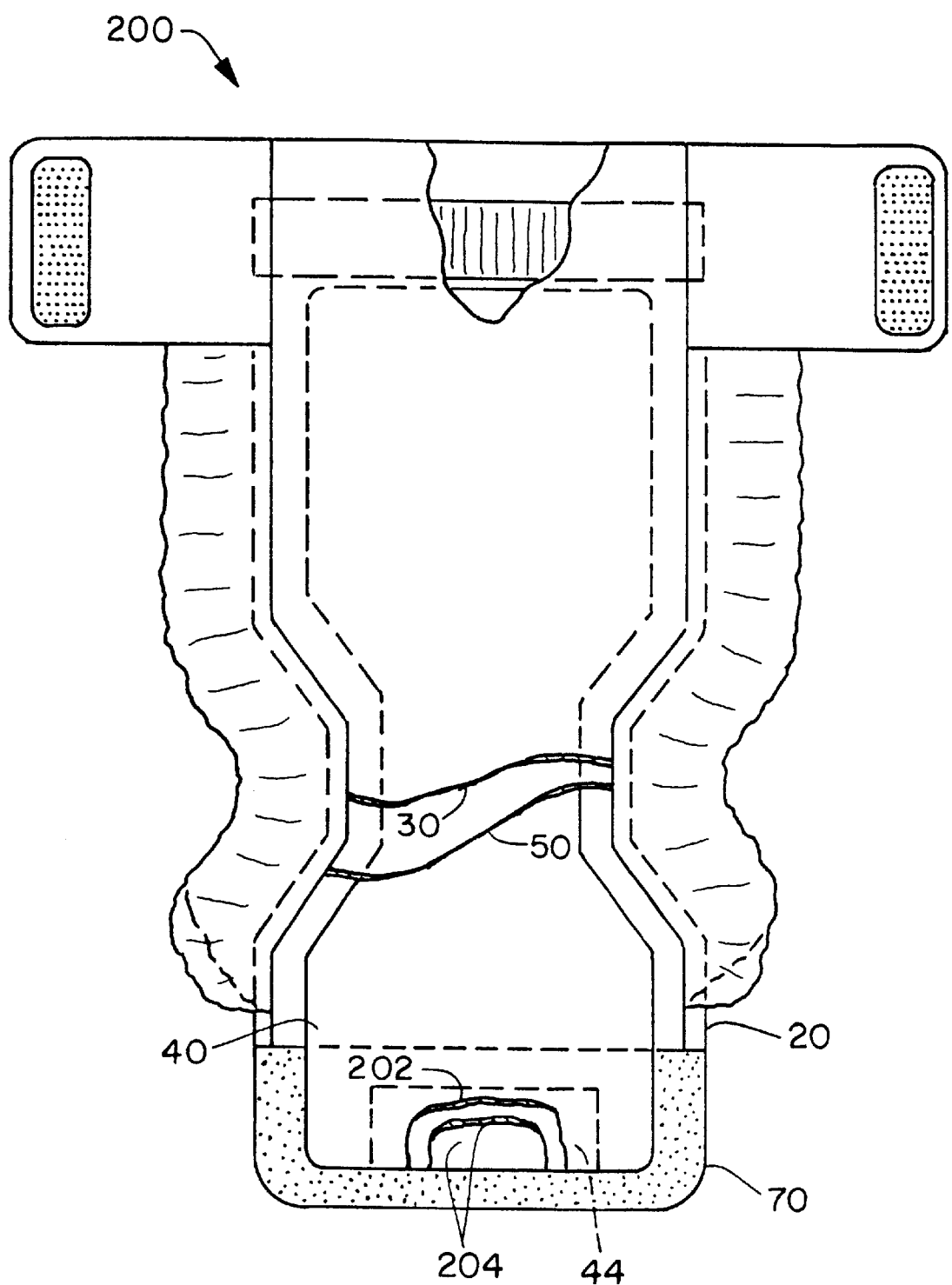
FIG. 10 representatively shows a partially sectioned view of an article having an absorbent body wherein the humidity transfer region is in the shape of a notch.

Humidity transfer zone 44 is located at a waistband section of absorbent body 40 and can be arranged in various suitable configuration. For example, the humidity transfer region may be constructed to extend from one longitudinal end of the absorbent body and span across the entire cross-directional width of the absorbent (FIGS. 3 and 7). The humidity transfer region may alternatively span only partially across the width of the absorbent body, as illustrated in FIGS. 8 and 10. In the embodiment of FIG. 10, the humidity transfer region occupies a generally rectangular notch-shaped area formed into absorbent body 40, but the occupied area may optionally be configured with any other suitable regular or irregular shape, such as the circle illustrated in FIG. 8.

In an optional configuration of the invention, absorbent body 40 can include a single aperture or a plurality of apertures 43 through the thickness dimension of the absorbent body, with at least a portion of the apertures located in operable registration with breathable panel 70 (FIG. 3). The apertures may, for example, be circular in shape with diameters within the range of about 0.5–2.0 cm. Apertures of other, different shapes may also be employed to provide an operable humidity transfer region to aid the operation of breathable panel 70.

Other components of diaper 10, such topsheet 30, separation layers (50, 52, 54) and other liquid management layers, may or may not extend over the area occupied by humidity transfer region 44. In the illustrated embodiment, these liquid-managing layers are configured to extend in a generally adjacent and facing relation with the humidity transfer region.

The article of the present invention can advantageously be constructed to reduce the excessive hydration of the wearer's skin and to reduce the relative humidity in the environment adjacent the wearer's skin. In a particular aspect of the invention, the breathable panel is constructed of a material which provides a Test Relative Humidity (TRH) value of not more than about 80%. Preferably, the breathable panel material is constructed to provide a TRH value of not more than about 75% to deliver improved performance. The reduced values of relative humidity can help allow the skin to dehydrate and recover towards its normal, ambient level of hydration.

In another aspect of the invention, diaper 10 can advantageously be constructed to provide for a mean net skin hydration value (mean net SHV) of not more than about 0.8 $gm/m^2$ in 2 min. Preferably, the diaper is constructed to provide a mean net SHV of not more than about 0.5 $gm/m^2$ in 2 min. for improved effectiveness. Such mean net SHV's are indicative of lower levels of skin wetness as compared to the excessive levels of skin wetness which can occur in conventional diapers after they have been wetted. The lower levels of skin wetness can help make the skin less susceptible to abrasion and less susceptible to chemical or biological irritants.

A suitable technique for determining the WVTR (water vapor transmission rate) value of a material is ASTM E96-80. For the purposes of the present invention, 3 inch diameter circular samples are cut out of the test material and out of a control material, CELGUARD® 2500 (Hoechst Celanese). Five samples are prepared for each material. The test dish is a No. 60-1 Vapometer pan distributed by Thwing-Albert Instrument Company, Philadelphia, Pa. One hundred milliliters of water are poured into each Vapometer pan, and each of the samples of the test materials and control material are placed across the open top area of an individual pan. Screw-on flanges are tightened to form a seal along the edges of the pans, leaving the associated test material or control material exposed to the ambient atmosphere over a 6.5 cm diameter circular area (an open, exposed area of about 33.17 $cm^2$). The pans are placed in a forced air oven set at 100° F. for 1 hour to equilibrate. The oven is a constant temperature oven with external air circulating through it to prevent water vapor accumulation inside. A suitable forced air oven is, for example, a Blue M Power-O-Matic 60 oven distributed by Blue M Electric Co. of Blue Island, Ill. Upon completing the equilibration, the pans are removed from the oven, weighed and immediately returned to the oven. After six hours, the pans are removed from the oven and weighed. The preliminary, test WVTR value is calculated as follows:

Test WVTR=(grams weight loss over 6 hours)×1263 (g/m$^2$/24 hours)

The relative humidity within the oven is not specifically controlled.

Under predetermined set conditions of 100° F. and ambient relative humidity, the WVTR for CELGUARD 2500 has been determined to be 5000 gm/m$^2$/24 hours. Accordingly, CELGUARD 2500 is run as a control sample with each test, and the preliminary test values are corrected to the set conditions using the following equation:

WVTR=(test WVTR/control WVTR)×5000 gm/m$^2$/24 hr.

CELGUARD 2500 is a 0.0025 cm thick film composed of a microporous polypropylene.

The Frazier Porosity values referred to in the present specification can be determined employing a Frazier Air Permeability Tester (Frazier Precision Instrument Co., Gaithersburg, Md.) and Method 5450, Federal Test Methods Standard No. 191A. For the purposes of the present invention, the test is conducted with a sample which measures 8 inches×8 inches.

Figure 4:
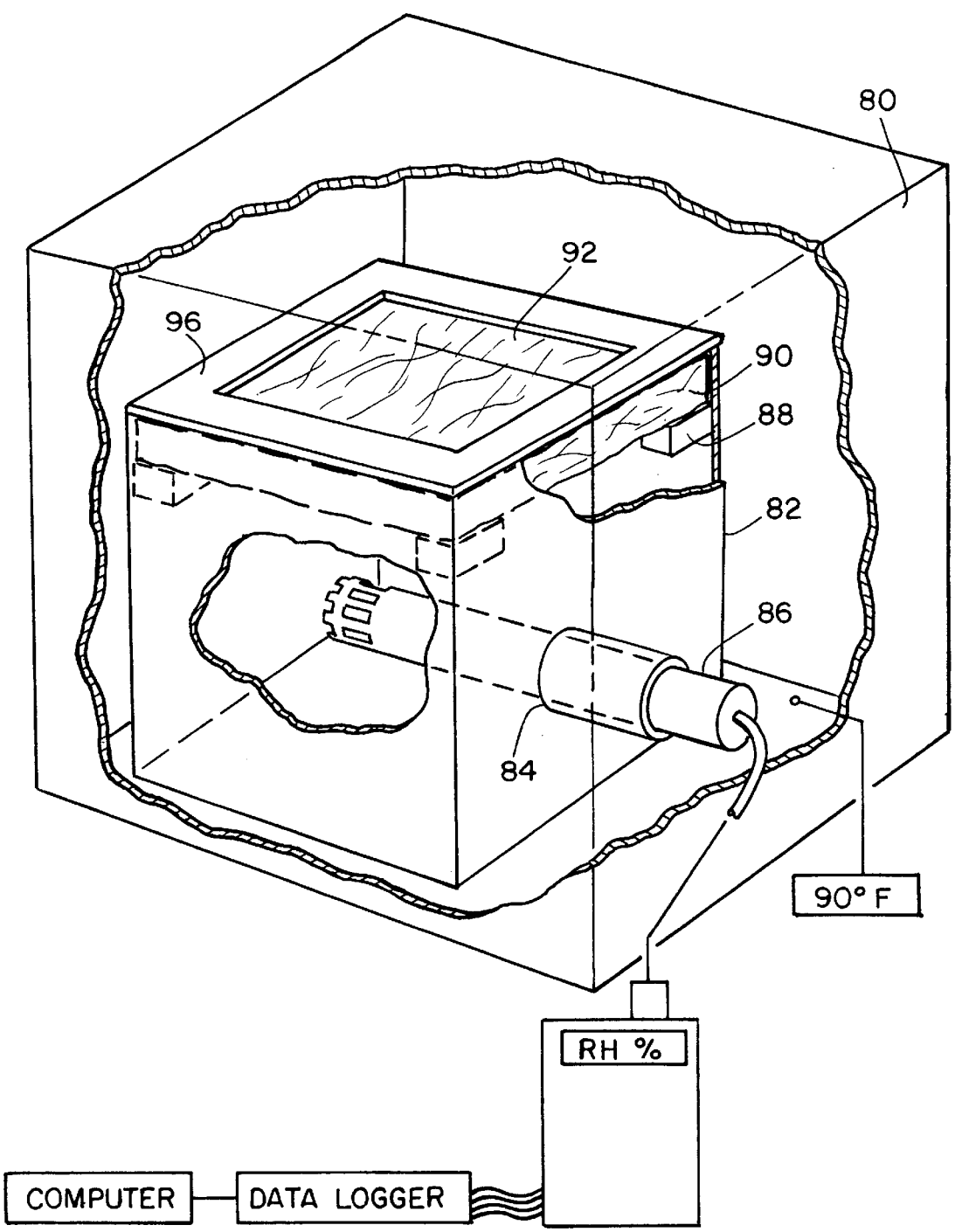
FIG. 4 shows a schematic, partially sectioned representation of an apparatus for measuring Test Relative Humidity values.

The Test Relative Humidity (TRH) value of a structure can be determined by employing the following TRH test apparatus and procedure:

As schematically shown in FIG. 4, the TRH test apparatus includes a temperature controlled chamber 80 and a relative humidity (RH) box 82. The temperature controlled chamber measures 18 inches×27 inches×36 inches to enclose a volume of about 10 cubic feet, and is maintained at a temperature of 90° F. The relative humidity within the chamber is dependent upon ambient conditions.

The RH box is open on the top and is made of ¼ inch thick plexiglass with outside dimensions of 4.5 inch×4.5 inch×5.5 inch and a volume of about 80 cubic inches when a sample is in place. The box may be partially filled with plastic spheres (0.75 inch diameter) to reduce the volume of air within the RH box. The box has a circular hole 84 on one side through which an RH probe 86 is inserted, and includes a narrow ledge 88 positioned approximately ¼ inch from the top edge. The test sample 92 is supported upon the ledge. The RH and temperature probes employed to measure and record relative humidity and temperature are manufactured by Solomat Corporation, Stamford, Conn. The particular instruments which can be employed are the MPM2000 Modular System with M2013 Modumeter, the MPM Data Logger, the 155RH Fast Response Probe for measuring relative humidity, and the PP206 SF Flexible Patch Thermocouple Probe for measuring temperature.

A sufficient number of 4 inch×4 inch absorbent squares 90 are prepared with each absorbent square composed of about 800 gsm basis weight wood pulp fibers and superabsorbent particles (about 15 weight percent super absorbent), such as particles of a polyacrylate superabsorbent. A tissue wrap composed of absorbent cellulosic material is placed on both sides of each absorbent square.

Samples of test materials 92 are cut into 5 inch×5 inch squares. An additional test sample composed of CELGUARD 2500 (Hoechst Celanese), which has a WVTR of 5000 grams/m$^2$/24 hours, is prepared and run as a control sample.

The relative humidity box, the Solomat relative humidity and temperature probes, the absorbent squares, the samples of test and control materials, and a quantity of isotonic saline (0.9 wt % sodium chloride) are allowed to equilibrate within the temperature control chamber.

A selected absorbent square is removed from the temperature control chamber, weighed and then placed back into the chamber. The temperature and relative humidity within the RH box are recorded, and the Solomat Data Logger is turned on to start recording relative humidity at one minute intervals. After two relative humidity data points are collected, the absorbent square and saline are removed from the chamber. An amount of saline equal to about 6 times the weight of the absorbent square is poured over the top of the absorbent square. The absorbent is then placed into the RH box, and a sample of test material is placed over the top of the box. A plexiglass holder 96 is employed to keep the sample on the box. The data logger reports relative humidity measurements at one minute intervals for sixty minutes, and the temperature inside the RH box is recorded. After the sixty minute test period, the sample of test material is removed, and the relative humidity and temperature inside the RH box are allowed to re-equilibrate with the chamber conditions before another sample is tested. When all of the samples have been tested, the data can be transferred from the data logger to a personal computer, printed and plotted. The test relative humidity (TRH) value for a particular sample is the relative humidity value measured at the sixty minute point.

Figure 5:
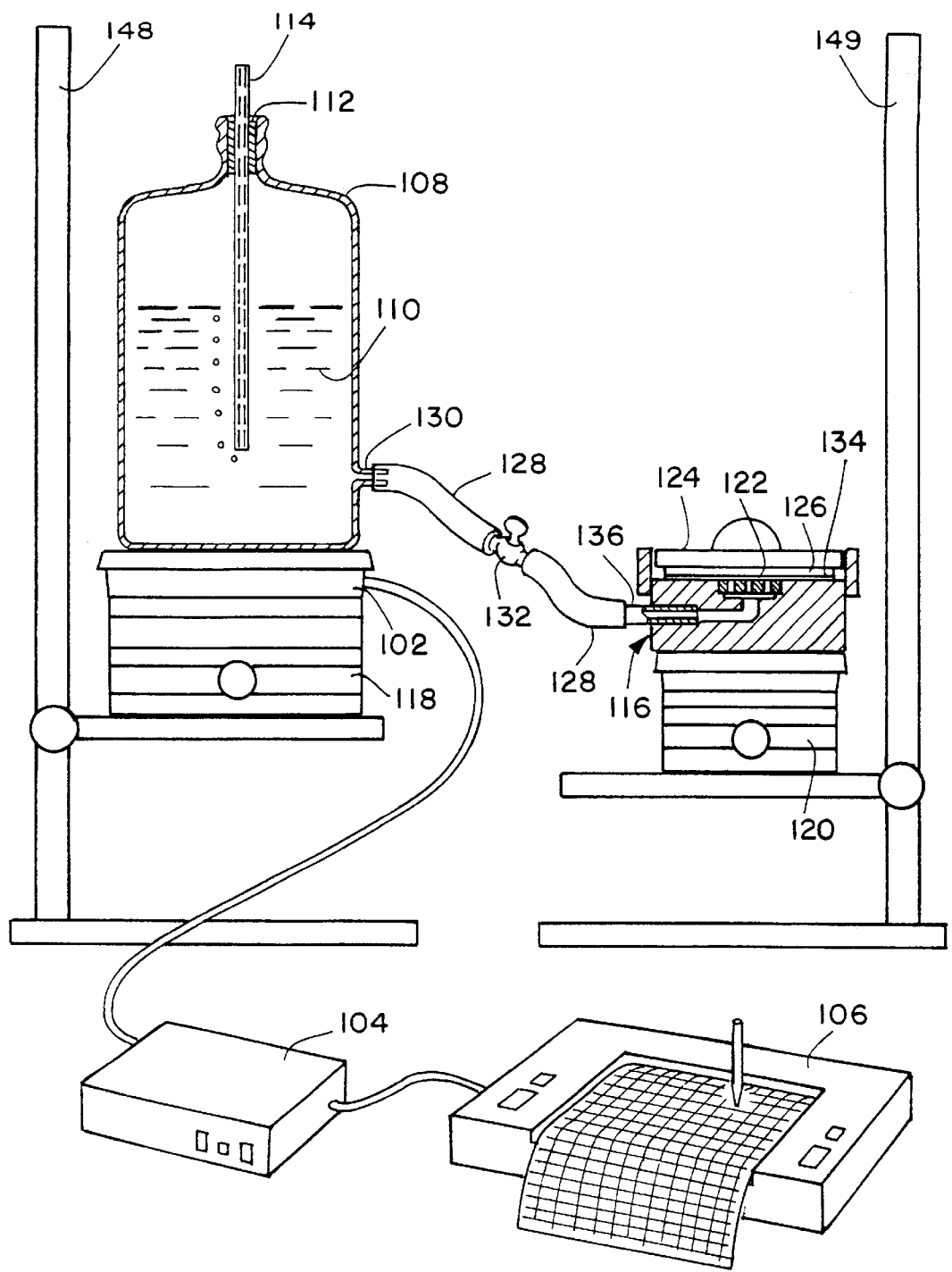
FIG. 5 representatively shows a partially sectioned apparatus for determining a Moisture Retention Index.

A suitable technique for determining the Moisture Retention Index of a section of absorbent body material is as follows:

With reference to FIG. 5, a suitable testing apparatus for determining Moisture Retention Index includes an electronic balance 102, which is accurate to 0.01 grams and has at least a 1000 gram capacity. In addition, the balance has a digital signal output for use with a digital-to-analog converter 104 and a chart recorder 106. A second electronic balance is employed to weigh the test samples. A suitable electronic balance, for example, is a Mettler PC2200 manufactured by Mettler Instrument Company, a business having offices located in Hightstown, N.J. The digital-to-analog converter should be compatible with electronic balance 102 and chart recorder 106. For example, in the illustrated embodiment, the digital-to-analog converter is a Mettler GC47 D/A Converter. A suitable chart recorder is, for example, a Fisher Recordall Series 5000, which is available from Houston Instrument, a company having offices located in Austin, Tex.

The apparatus further includes a 500 milliliter aspirator bottle 108 for holding a suitable reservoir supply of synthetic urine 110. The aspirator bottle is configured with a size number 4 rubber stopper 112 and a 7 inch glass air tube 114 which has an inside diameter of 0.22 inches (5.58 mm). Air tube 114 is positioned through a bore hole formed through the center of stopper 112, and is inserted until approximately 5 inches of the air tube protrudes from the inside surface of the stopper.

Figure 5A:
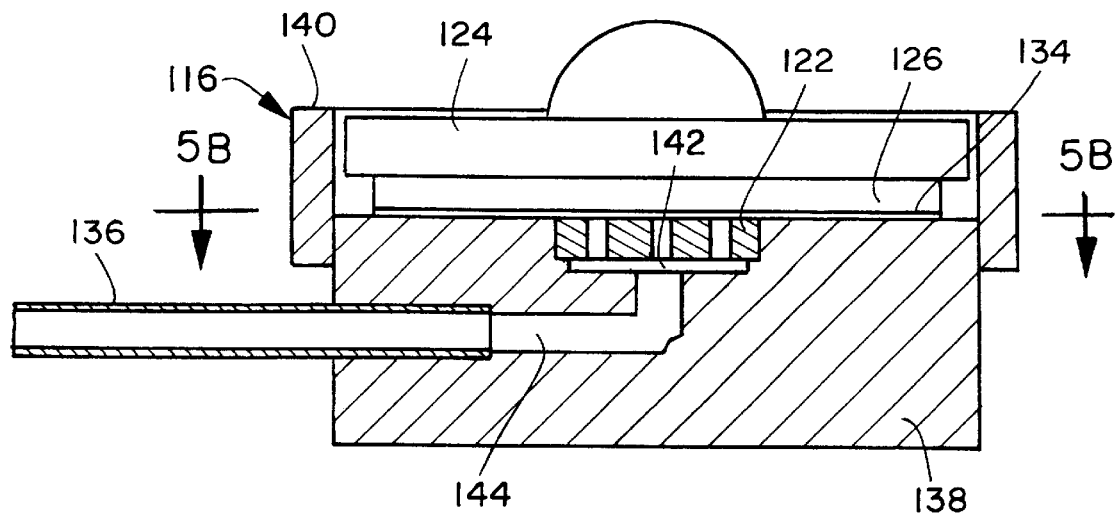
FIG. 5A representatively shows a partially sectioned, side view of an absorbency test chamber.
Figure 5B:
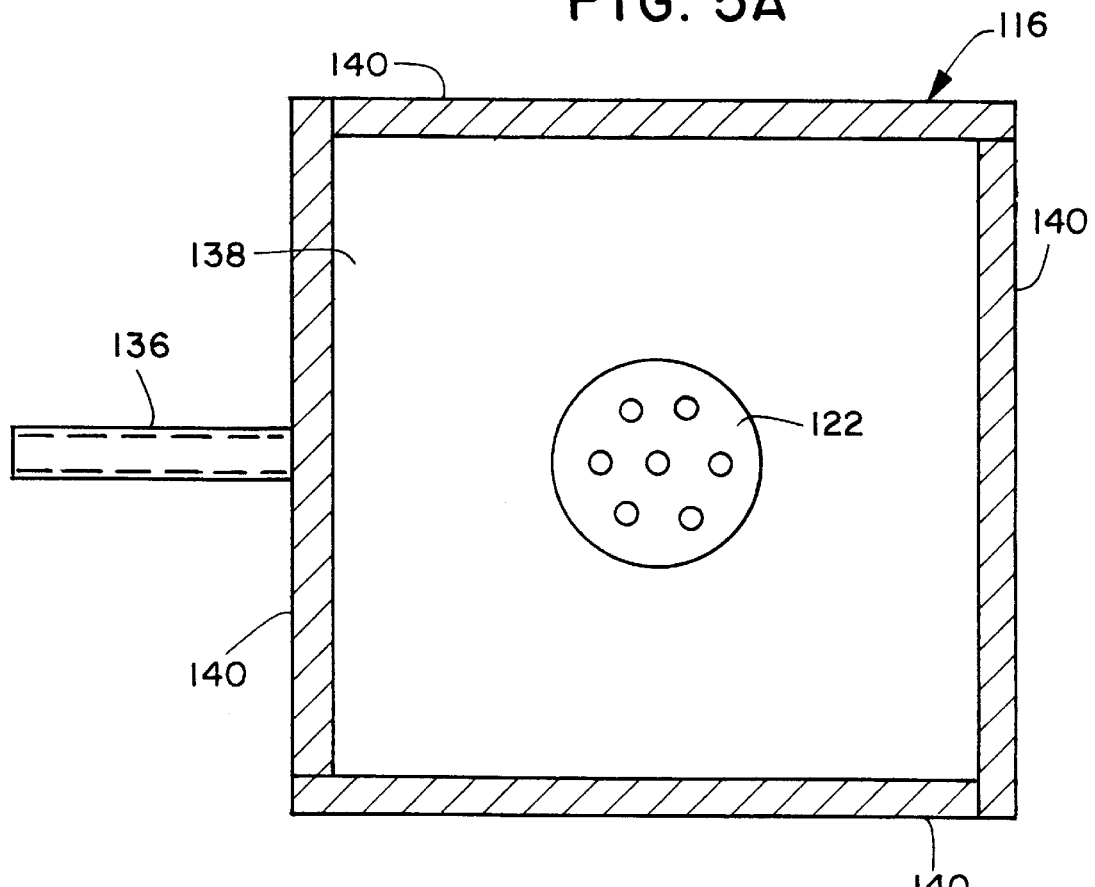
FIG. 5B representatively shows a top view of an absorbency test chamber with its cover removed.

An enlarged partially sectioned, side view of the absorbency test chamber 116 is representatively shown in FIG. 5A, and an enlarged top view of the absorbency test chamber, with its cover removed, is representatively shown in FIG. 5B. The test chamber is composed of a suitable material, such as LUCITE material, and has a substantially square base area measuring 4 inches by 4 inches. The chamber includes a 4 in×4 in base member 138, and a ⅝ inch (about 1.59 cm) high wall member 140 situated along each of the four sides of the base member. A 125 gram cover 124 is configured for placement over the sample placed within chamber 116. The cover extends over a generally square area and is configured to be slightly smaller than the top opening into chamber 116. Accordingly, the cover can sufficiently prevent the evaporation of moisture, and can readily slip along the walls of the chamber to provide a selected pressure onto the top of a sample placed therein. A stepped, circular recess 142 is formed into the top of base 138, and conduit 144 extends through the base to a 0.25 inch inside diameter outlet tube 136. Conduit 144 conducts liquid into the bottom of recess 144 where it is then transmitted through a multiport transfer disk to a test sample 126. Within the test chamber, a 1.25 inch diameter multiport plate 122 composed of lucite sits in recess 142 resting on top of the step therein. The multiport plate includes 7 ports, each being 3 mm in diameter, with one port located in the center of plate 122 and the remaining six ports arranged radially from the center port and equally spaced circumferentially around the center port along a 1 3/16 inch (about 3.016 cm) diameter circle. The seven ports are positioned 3/8 inch apart center-to-center, and plate 122 is centrally located within chamber 116. Plastic tubing having a 0.25 inch inside diameter, such as TYGON tubing—R3603, interconnects outlet tube 130 of reservoir bottle 108 and tube 136 which enters base 138. Plastic tubing 128 has an approximate total length of 7.5 feet, but the exact lengths are not critical. The tubing lengths should allow for easy use of the apparatus, but should not be excessive. A control valve, such as a two-way polypropylene stopcock 132, regulates the liquid flow through plastic tubing 128. Stopcock 132 has a bore size of 4 millimeters so as not to excessively restrict liquid flow. Laboratory jacks are employed to regulate the vertical positioning of the components of the testing apparatus. In particular, laboratory jack 118 supports electronic balance 102 and reservoir bottle 108, while laboratory jack 120 supports test chamber 116 and the components contained therein. Laboratory stands 148 and 149 can be employed to make any large, coarse adjustments of the vertical positions of the components of the testing apparatus.

The testing apparatus should be clean and free from bacterial contamination and salts which may have settled out of the synthetic urine. During testing, the test equipment should not be handled. If the tubing is removed or handled, an equilibration time of approximately 1 hour should be employed to allow relief of any stresses imparted to the tubing. This equilibration time should also be allowed when refilling reservoir bottle 108. The tubing should not be touched during testing. The absorbent material being tested should be preconditioned at "standard" conditions of 50±2% RH and 23±1 degrees Centigrade. The appointed body side of the absorbent material should be positioned facing multiport plate 122. Any detergents employed to clean any components of the test apparatus should be completely removed so as not to affect the surface tension of the synthetic urine employed to conduct the tests.

Prior to testing, reservoir bottle 108 is filled with synthetic urine and a portion of the liquid is drained through the tubing to completely remove all air bubbles from the tubing and from the fluid conduits in the testing apparatus. The drained synthetic urine is discarded and the stopcock is closed to stop the flow of liquid. The reservoir bottle is then refilled. Plastic tubing 128 should be free of sharp bends or kinks which might impede the flow of liquid and alter the test results.

Prior to testing, the equipment is also adjusted to establish a zero head. First, chamber 116 is leveled by placing an suitably sized bubble level indicator in the center of the chamber and by pushing slightly on the appropriate side of laboratory jack 120. The front and back of chamber 116 should also be leveled. At this point, testing chamber 116 may be taped in place on laboratory jack 120. Stopcock 132 is then opened to permit liquid flow, and a slightly concave meniscus is created in each of the seven 3 mm ports in plate 122 by adjusting the height of laboratory jack 120. Zero head is obtained when each of these ports contains synthetic urine with a slightly concave meniscus, and an air bubble is maintained at the bottom of glass tube 114 within reservoir bottle 108. Stopcock 132 is then closed to stop the flow of liquid and chamber 116 is checked to make sure that it is still level. The apparatus is then allowed to equilibrate for 3–6 hours. This equilibration time is not necessary when the testing apparatus is in continuous use and the liquid has not been changed or added. Chart recorder 106 is turned on and adjusted to plot at zero when the electronic balance 102 is at its zero setting.

The equilibrium setting of the testing apparatus is checked by placing cover 124 on chamber 116 and closing stopcock 132. Electronic balance 102 is then zeroed and the chart recorder is turned on. The testing apparatus is at equilibrium if the absorbed fluid weight reading is stable at zero. Preferably, the absorbed fluid weight reading should not vary by more than plus or minus 0.03 grams in 15 minutes.

Test sample 126 is configured in the shape of a 3 inch diameter disk. The sample is weighed to the nearest 0.01 gram and the weight is recorded. The thickness of the sample is measured with a 3 inch (7.62 cm) diameter platen under a restraining pressure of 0.2 psi (1.38 kPa).

A 3 inch diameter piece of filter paper, such as Whatman No. 4 filter paper, is centered over multiport plate 122 within chamber 116. Stopcock 132 is then opened to wet out the filter paper and remove all air bubbles. It should be noted that a new piece of filter paper is used for each test sample. The stopcock is then closed to stop the flow of liquid, and excess fluid is blotted from the edges of the filter paper. The center of the filter paper, however, is not blotted so as to avoid forming any air bubbles. The areas around filter paper 134 and cover 124 should both be dry. Stopcock 132 is opened and electronic balance 102 is zeroed out once it stabilizes.

The test is started by simultaneously placing and centering absorbent sample 126 over filter paper 134 with cover 124 resting on top of the sample, and turning on the chart recorder 106. Test sample 126 is then allowed to absorb fluid for a 30-minute testing period. At the end of this period, stopcock 132 is closed and chart recorder 106 is turned off. The final reading of the electronic balance is recorded on the chart paper to serve as a check of the chart recorder data. The Moisture Retention Index is the grams of synthetic urine absorbed by test sample 126 during the 30-minute test period.

Figure 6:
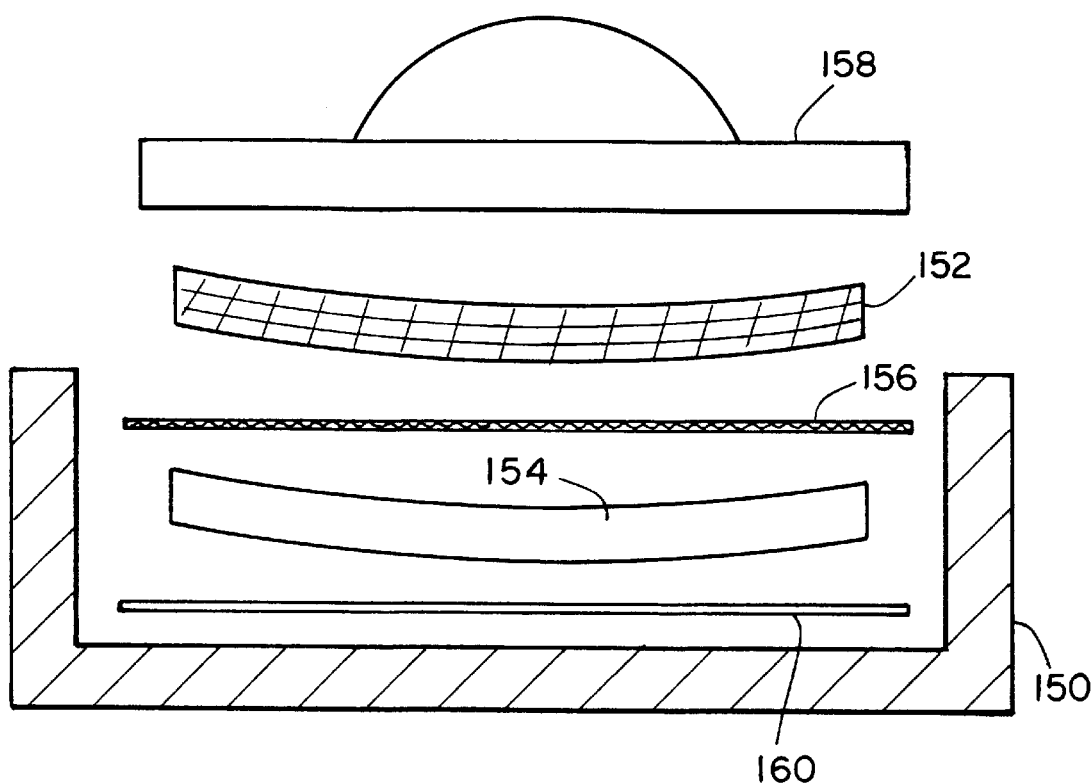
FIG. 6 representatively shows a partially sectioned apparatus for determining a Wicking Index.

A suitable technique for determining the Wicking Index of a single, generally homogeneous material or of a composite material is as follows:

With reference to the apparatus representatively shown in FIG. 6, the Wicking Test apparatus includes a chamber 150 having a 4 inch by 4 inch base measurement. A 3 inch diameter test sample 152 is weighed employing an electronic balance such as a Mettler PC2200 balance which is accurate to 0.01 gram. A 4 inch by 4 inch piece of 1.0 mil thick polyethylene film 160 is placed on the bottom of chamber 150, and a 3 inch diameter piece of retention material 154 is placed on top of the polymer film. The retention material is composed of 3 layers of coform fibrous web material and superabsorbent particles. Each layer of coform material is composed of woodpulp fluff and 2 wt % meltblown polypropylene fibers. Contained within the coform material are about 1.69 grams (range: 1.64–1.73 grams) of the superabsorbent material. The resultant retention material 154 has a total thickness of 0.75 inches and a total basis weight of 1060 grams per square meter. The total dry weight of the retention material is about 4.84 grams (range: 4.70–4.95 grams), of which 35 weight percent is superabsorbent material. The particles of superabsorbent material are composed of polyacrylate hydrogel polymer, such as SANWET IM-5000 manufactured by Hoechst Celanese.

After loading the retention material with 24.2 gm (ml) of synthetic urine (5 gram/gram liquid loading), a 4 inch by 4 inch piece of screen material 156 is placed on top of retention material 154. The screen material is a fiberglass mesh screen having the screen strands arranged in a generally square-grid pattern with 18 openings per lineal inch (324 openings per square inch) and a screen thickness of about 0.028 cm.

Test sample 152 is then placed on top of screen 156 and a 125 gram cover 158 is placed on top of the entire test sample 152 to impart a pressure of 0.039 psi. The cover extends over a generally square area and is configured to be slightly smaller than the top opening into chamber 150. Accordingly, the cover can sufficiently prevent the evaporation of moisture, and can readily slip between the walls of the chamber to provide the selected pressure onto the top of a sample placed therein. Thirty minutes after placing weight 158 on top of test sample 152, the test sample is removed from chamber 150 and weighed to the nearest 0.01 gram. The difference between the dry sample weight and the "wet" sample weight after the 30 minute testing period is the amount of fluid "wicked" from the loaded retention material 154 into test sample 152. The amount of wicked liquid (in grams) is referred to as the Wicking Index.

Skin hydration values are determined by measuring total transepidermal water loss (TEWL), and can be determined by employing the following test procedure:

The test is conducted on partially toilet trained infants who have no lotions or ointments on the skin and have not been bathed within 2 hours prior to the test. Half of the selected group of infants is appointed to wear the test diaper first, and the control diaper second. The other half of the group of infants is appointed to wear the control diaper first, and the test diaper second.

Each test diaper is weighed before and after use to verify the volume of liquid added into the diaper. A felt tip pen is employed to mark an "X" at the target zone inside the diaper, with the "X" positioned 3 inches below the top front edge of the absorbent pad and centered side-to-side. The TEWL measurements are taken with an evaporimeter, such as an Evaporimeter EP1 instrument distributed by Servomed AB, Stockholm, Sweden. Each test measurement is taken over a period of two minutes with TEWL values taken once per second (a total of 120 TEWL values). The digital output from the Evaporimeter EP1 instrument gives the rate of transepidermal water loss (TEWL) in g/m²/hr. Skin hydration values (SHV) are in units of total amount of water loss per unit area measured during the two minute sampling period, and are calculated as follows:

$$SHV(gm/m^2 \text{ in 2 min}) = \sum_{n=1}^{120} (TEWL)_n \times \frac{1}{120} \times \frac{1 \text{ hr}}{60 \text{ min}} \times 2$$

A preliminary skin hydration value measurement is taken on the infant's lower abdomen in a region corresponding to the target zone of the diaper using the evaporimeter for the purpose of establishing the initial skin hydration value of the infant's skin at the diaper target zone. A diaper is then placed on the infant. Prior to securing the diaper on the infant, a tube is positioned to direct a flow of liquid to hit the premarked target zone. Once the diaper is secured, 120 milliliters of adjusted saline (surface tension adjusted to 55 dynes/cm using TWEEN 20) is added in two insults of 60 milliliters each at a rate of 15 milliliters/second. The time between insults is 30 seconds.

The infant wears the diaper for 30 minutes after which two skin hydration measurements are taken. A base-line measurement is taken at the upper thigh in a region of skin not covered by the diaper. This base-line SHV is compared with the preliminary SHV measurement to establish that the infant is not perspiring. The presence of perspiration can cause the SHV measurement to be artificially high. A test measurement of skin hydration is also taken on the lower abdomen corresponding to the target zone mark of the diaper. The used diaper is then weighed, and the infant is allowed to play in his/her cloth underwear for 25–30 minutes. The test procedure is then repeated for each infant using the diaper type (test or control) which the infant has not yet worn.

The control diaper provided a standardized basis for comparing the performance of the diaper configuration being tested and evaluated. In the tests conducted for the purposes of the present invention, the control diaper included an outer cover backsheet composed of 1 mil thick polypropylene, and a topsheet layer composed of a spun-bonded polypropylene nonwoven fibrous web having a basis weight of 27 gsm. The topsheet included 0.206 cm (0.081 in) diameter apertures formed therethrough across a central region of the topsheet at a frequency of about 76 apertures per square inch. The central region extended over a width of 3.5–5 inch and extended along the full length of the diaper. An absorbent pad was located between the backsheet and topsheet layers, and was composed of woodpulp fluff which had a basis weight of about 800 gsm and included about 15 wt % polyacrylate superabsorbent polymer particles. The pad also included a tissue wrap comprising an absorbent layer of cellulosic creped wadding material. A liquid transport layer was positioned between the topsheet and the absorbent pad, and was composed of a nonwoven spunbond fibrous web of polypropylene fibers having a basis weight of about 42 gsm. The control diaper was secured to the infant with adhesive tape fasteners, and included elasticized gathers at the leg and waist regions of the diaper.

Data is discarded for any infants which have added to the loading of saline solution. The value reported for the mean net SHV (grams/m² in two minutes) is the arithmetic mean for all infants of the post-wear skin hydration value taken at the lower abdomen (target zone mark) minus the skin hydration value measured at the upper thigh.

The net skin hydration value is determined as follows:

Net $SHV_i = Y - Z$

Where:

Y=skin hydration value measured at target zone mark of an individual infant

Z=baseline skin hydration value measured at leg, upper thigh of individual infant $SHV_i$=skin hydration value for individual infant Then, $$\text{Mean Net } SHV = \frac{\sum_{i=1}^{N} \text{Net } SHV_i}{N}$$

Where: N=number of infants in study
The percent reduction in skin hydration is determined as follows:

$$\% \text{ Reduction} = \frac{\sum_{i=1}^{N}[((C-D)/C)\times 100]}{N}$$

Where:
C=Net $SHV_1$ for control diaper
D=Net $SHV_i$ for test diaper
N=number of infants in study The following examples are presented to provide a more detailed understanding of the invention. The specific materials and parameters are exemplary, and are not intended to specifically limit the scope of the invention.

EXAMPLE 1

A disposable diaper was produced, comprising a backsheet layer that had a base section which was liquid and vapor impermeable, and an attached panel section which was liquid impermeable but vapor permeable. An absorbent body was sandwiched between a liquid permeable topsheet layer and the backsheet layer, and separation layers were located between the absorbent body and the topsheet layer. The diaper also included a hook and loop fastening system.

The base portion of the backsheet comprised a conventional, 1 mil thick polyethylene film which was liquid and vapor impermeable. The breathable panel was attached to extend from the end of the base portion, and formed the front waistband section of the backsheet. The material used for the breathable panel was a laminate composed of 34 gsm calendered fine fiber polypropylene meltblown, and 24 gsm polypropylene spunbond which was thermally bonded with an approximately 12% bond area. The meltblown side of the fabric was next to the absorbent body, and the spunbond side was positioned to the outside of the diaper. This fabric material had a WVTR of approximately 5000 g/m²/24 hours. The breathable panel extended the full width of the diaper and extended longitudinally approximately 13 cm from the front edge of the diaper.

The absorbent body was composed of a mixture of woodpulp fluff and polyacrylate superabsorbent particles. The basis weight of the fluff was about 800 gsm and the mixture contained about 15 wt % superabsorbent particles. In addition, the absorbent body included a tissue wrap of high wet-strength tissue.

The topsheet layer was configured for placement against the body of the wearer. Accordingly, the topsheet material was soft and nonirritating, and was composed of a 27 gsm polypropylene spunbond nonwoven fabric.

In the hook-and-loop fastening system, the loop material was applied to the breathable panel 70 using adhesive only around the edges of the material to prevent occlusion of the breathable panel.

The separation layers were three layers of 42 gsm polypropylene spunbond (total 126 gsm) providing a combined bulk thickness of 0.11 cm (measured at a pressure of .207 kPa) and a bulk density of 0.11 g/cc. The separation layers were 12.7 cm wide and were 16.5 cm in length with the front edge of the layers located 5 cm from the front edge of the absorbent. The layers were ultrasonically spot bonded to each other and to the topsheet at intervals of approximately 5 cm around the edges of the layers.

The diaper exhibited a mean net SHV of about 0.3 grams/m² in two minutes. This represented a 69% reduction in skin hydration, as compared to the conventional control diaper described herein above.

EXAMPLE 2

A diaper was produced comprising a backsheet that had a base section which was liquid and vapor impermeable, and an attached panel section which was liquid impermeable but vapor permeable. An absorbent body was sandwiched between the backsheet and a liquid permeable topsheet layer, and separation layers were located between the absorbent body and the top sheet.

The base portion of the backsheet comprised a conventional, 1 mil thick polyethylene film which was both liquid and vapor impermeable. The breathable panel was attached to and extended from the end of the base portion, and formed the front waistband section of the backsheet. The material employed to construct the breathable panel was a 34 gsm calendered fine fiber, polypropylene meltblown nonwoven fabric. This fabric had a WVTR of approximately 5000 gm/m²/24 hrs. The breathable panel extended the full width of the diaper and extended longitudinally approximately 13 centimeters from the front edge of the diaper.

The separation layers comprised three layers of 42 gsm polypropylene spunbond (total 126 gsm) with a combined bulk thickness of 0.11 cm (measured at a pressure of 0.207 kPa) and a bulk density of 0.11 gm/cc. The separation layers were 12.7 cm wide, and were 16.5 cm in length with the front edge of the separation layers located 5 cm from the front edge of the absorbent body. The separation layers were ultrasonically spot bonded to each other and to the top sheet at intervals of approximately 5 cm around the edges of the layers.

The diaper exhibited a mean net SHV of about 0.2 gm/m² in two minutes. This represented a 70% reduction in skin hydration, as compared to the conventional control diaper.

EXAMPLE 3

This article was the same as in Example 2, except that the separation layers were 24 cm in length with the front edge of the layers located at the front edge of the absorbent body.

The diaper exhibited a mean net SHV of about 0.45 gm/m² in two minutes. This represented a 56% reduction in skin hydration, as compared to the control diaper.

EXAMPLE 4

This article was the same as in Example 3, except that the separation layers were a polyester bonded-carded-web obtained from H.D.K., a company located in Rogersville, Tenn. The web was composed of fibers which had a denier of about 5.5 and were bonded together with approximately 16.6% powder adhesive. The combined basis weight of the three layers was about 108 gsm, the combined bulk thickness was 0.40 cm and the combined bulk density was 0.03 g/cc.

The diaper exhibited a mean net SHV of about 0.6 gm/m² in two minutes. This represented a 52% reduction in the mean net SHV, as compared to the control diaper.

EXAMPLE 5

A diaper was produced, comprising a backsheet layer that had a base section which was liquid and vapor impermeable, and an attached panel section which was liquid impermeable but vapor permeable. An absorbent body was sandwiched between the backsheet and a liquid permeable topsheet layer.

The base portion of the backsheet comprised a conventional, 1 mil thick polyethylene film which was liquid and vapor impermeable. A breathable panel was attached to and extended from the end of the base portion, and formed the front waist band section of the backsheet. The breathable panel was composed of a 34 gsm calendered fine fiber polypropylene meltblown nonwoven fabric. This fabric had WVTR of approximately 5000 gm/m$^2$/24 hrs. The breathable panel extended the full width of the diaper and extended longitudinally approximately 13 cm from the front edge of the diaper.

The diaper exhibited a mean net SHV of about 0.5 gm/m$^2$ in two minutes. This represented a 40% reduction in skin hydration, as compared to the control diaper.

EXAMPLE 6

This article is the same as in Example 1, except that the separation layers extend from the front waist edge of the absorbent body to the rear waist edge of the absorbent.

EXAMPLE 7

This article is the same as in Example 6, except that the separation layers are composed of a polyester bonded-carded-web manufactured by H.D.K. The web is composed of fibers having a denier of about 5.5 d bonded together with approximately 16.6% powder adhesive. The combined basis weight of the three separation layers is about 103 gsm, the combined bulk thickness is about 0.09 cm, and the combined bulk density is about 0.12 gm/cc.

EXAMPLE 8

A diaper is produced, comprising a backsheet that was liquid and vapor impermeable; a liquid permeable topsheet layer; an absorbent body located between the topsheet layer and backsheet layer; and separation layers located between the absorbent body and the topsheet layer.

The separation layers are three layers of 42 gsm (each layer, total 126 gsm) polypropylene spunbond with a combined bulk thickness of 0.11 cm and a bulk density of 0.11 g/cc. The separation layers are 12.7 cm wide and extend the full length of the absorbent body.

EXAMPLE 9

This article is the same as in Example 8 except that the separation layers are composed of a woven cotton material having a bulk thickness of 0.076 cm, a bulk basis weight of 186 gsm, and a bulk density of 0.245 g/cc. Because this cotton material has about the same hydrophilicity as the material comprising the absorbent body, the separation layers can hold liquid close to the skin, and result in skin hydration values greater than that measured without the separation layers present.

EXAMPLE 10

This article is the same as in Example 6, except that the breathable panel is comprised of a polyethylene microporous film such as PMP-1 from Mitsui Toatsu. This film material has a WVTR of approximately 4000 g/m$^2$/24 hours.

EXAMPLE 11

This article is the same as in Example 6, except that there are breathable panels at both the front waistband section and back waistband section of the diaper.

EXAMPLE 12

This diaper is the same as in Example 6, except that the entire backsheet is composed of a vapor permeable material, such as PMP-1 from Mitsui Toatsu, having a WVTR of approximately 4000 g/m$^2$/24 hours. The diaper can exhibit a cold and clammy feel when moisture is evaporating through the backsheet 20.

EXAMPLE 13

This article is the same as in Example 6, except that it includes a humidity transfer region. This is accomplished by making the area of the absorbent body which is behind the breathable panel either less dense than the rest of the absorbent body or with apertures through the thickness of the absorbent.

EXAMPLE 14

A diaper garment 200 representatively shown in FIG. 7 includes a backsheet layer 20, a topsheet layer 30, and an absorbent body 40 interposed between the backsheet and topsheet layers. Back sheet 20 includes a breathable panel 70 which is connected to provide an extension of the backsheet layer. Absorbent body 40 includes a humidity transfer region 44 which is connected to extend from a longitudinal end of the absorbent body. Optionally, one or more separation layers 50 may be located between absorbent body 40 and topsheet 30.

In the illustrated embodiment, absorbent body 40 is an absorbent composite comprising a surge control layer 202, a tissue layer 204, and a retention portion 206. Surge layer 202 is a fibrous material which quickly collects and temporarily holds rapid discharges of liquid, and transports the liquid from the initial entrance point to other parts of the absorbent body. The representatively shown embodiment of surge layer 202 is composed of a HYDROFIL material in the form of a macrofiber, meltblown, nonwoven fibrous web having a basis weight of 200 gsm and a bulk thickness of 0.086 inches (at 0.2 psi). The HYDRORIL material is available from Allied-Signal, a company having offices located in New York, N.Y. Alternatively, surge layer 202 may comprise a nonwoven web of polyethylene fibers having a web basis weight of 200 gsm and a bulk thickness of 0.72 inches (at 0.2 psi).

The illustrated embodiment of retention portion 206 comprises 3 layers of a nonwoven coform web and particles of superabsorbent material. The superabsorbent material is composed of a polyacrylate hydrogel polymer and comprises 35 weight percent of the retention portion. The coform layers had a total basis weight of 900 gsm and a total bulk thickness of 0.75 inches (at 0.2 psi). The coform material is composed of 50–63 weight percent wood pulp fluff and 2–15 weight percent of meltblown HYDROFIL fibers or meltblown polypropylene fibers. High wet strength tissue 204 has a basis weight of 21 gsm and a bulk thickness of 0.009 inches.

The front waistband of the absorbent body of the diaper includes a humidity transfer region 44 comprising a substantially hydrophobic, nonwettable, polyester fiberfill material, a material ordinarily employed for pillow batting. The fiberfill material has a basis weight of about 180 gsm and a density of about 0.0417 g/cc (at 0.2 psi). The humidity transfer region measures 1 in along the diaper length dimension and 4.5 in along the diaper cross-direction, thus covering an area of 4.5 in$^2$.

A vapor permeable panel 70 placed over the humidity transfer region is a composite composed of an inner layer of calendered meltblown fibers and an outer layer of Guilford knit fabric. In the illustrated embodiment, the Guilford fabric is Guilford part 19903 loop material, which is a warp knit polyester fabric of two-bar construction. The fabric is composed of 40/13 polyester yarn (front bar) and 20 denier per filament monofilament (back bar) sprayed with Rohm & Haas AC-73 binder material. The knit fabric has a basis weight of 3.2 ounces per square yard, and is available from Guilford Mills, a company having offices in Greensboro, N.C. The binder material is available from Rohm & Haas Company, a business having offices in Philadelphia, Pa.

EXAMPLE 15

A diaper garment was constructed with the structure described in Example 14. The diaper of this Example, however, included a topsheet composed of a layer of Guilford 19903 knit fabric, and included a separation layer composed of another layer of Guilford 19903 knit fabric placed adjacent the topsheet.

When compared to a standard control diaper, the diaper constructed in accordance with this Example exhibited a 43% decrease in skin hydration value.

EXAMPLE 16

A diaper garment was constructed with the structure described in Example 15. The diaper, however, was modified to include a humidity transfer region having the form of a 2 in diameter hole formed in the SAM/fluff (liquid retention material) of the absorbent body, as representatively shown in FIG. 8. The hole was positioned with the edge of the hole located about 1 inch from the adjacent waistband edge of the absorbent body, and the removed liquid retention material was replaced with a polyester fiberfill material having a basis weight of about 180 gsm basis weight and a bulk thickness of about 0.17 in (about 0.43 cm), as measured at 0.2 psi. When compared to a standard control diaper, the diaper of this Example exhibited a 27% decrease in skin hydration value.

EXAMPLE 17

Figure 9:
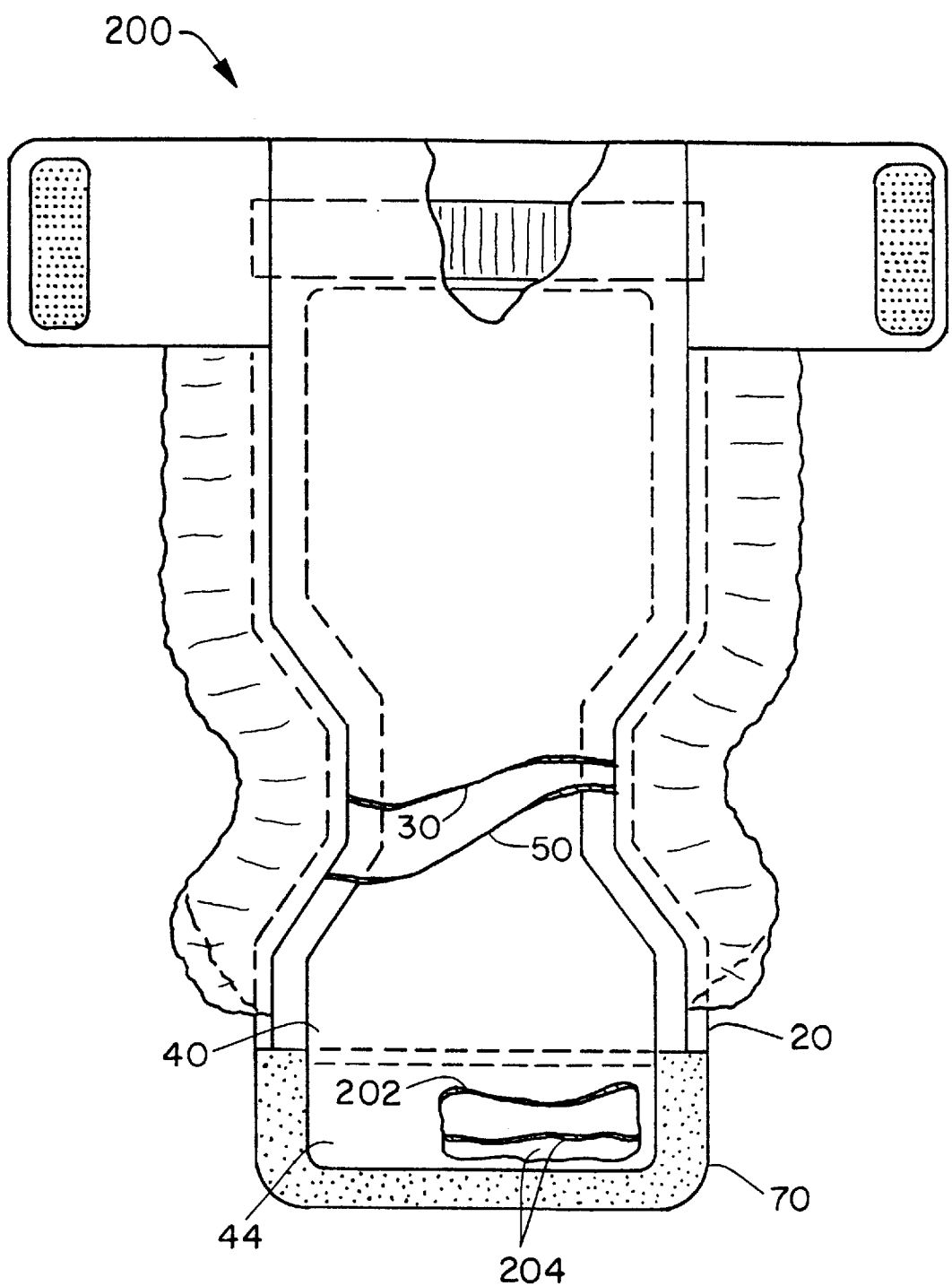
FIG. 9 representatively shows a partially sectioned view of another article which includes an absorbent body having a humidity transfer region composed of a multi-layer composite.

A diaper garment is constructed with the structure described in Example 15. The diaper of this Example, however, was modified to include a humidity transfer region comprising a multilayer composite composed of a 200 gsm layer of HYDROFIL surge material having a thickness of 0.086 inches, and 2 layers of 21 gsm tissue material, as representatively shown in FIG. 9. When compared to a standard control diaper, the diaper constructed in accordance with this example exhibited a 41% decrease in skin hydration value.

EXAMPLE 18

A diaper garment was constructed with the structure described in Example 15. The diaper of this Example, however, was modified to include a humidity transfer region having the form of a generally rectangular notch formed in absorbent body 40. At the location of this notch, the humidity transfer region was composed of a 200 gsm web of meltblown polyethylene fibers having a thickness of 0.072 inches and 2 layers of 21 gsm tissue material, as representatively shown in FIG. 10. The humidity transfer region had an area of 2.5 square inches. When compared to a standard control diaper, the diaper of this example exhibited a 29% decrease in skin hydration value.

EXAMPLE 19

An absorbent composite was constructed with 2 layers of Guilford 19903 loop material. Each layer had a basis weight of 108 gsm and a bulk thickness of 0.026 inches (at 0.2 psi). The Guilford loop material provided the topsheet component of the absorbent composite. Overlying the layers of Guilford loop material was 2 layers of HYDROFIL surge material. Each of these layers of surge material had a basis weight of 200 gsm and a bulk thickness of 0.086 inches (at 0.2 psi). Overlying the layers of surge material was a 21 gsm layer of tissue material. A layer region of retention material was located over the tissue material and formed the outermost portion of the absorbent composite. The retention material was composed of 3 layers of coform material containing 35 weight percent of superabsorbent particles. The coform material had a total basis weight of 900 gsm and a total bulk thickness of 0.75 inches (at 0.2 psi).

WVTR testing of samples of the absorbent composite material loaded with different amounts of synthetic urine produced the following data:

| Load (g/g) | WVTR (g/m$^2$ per 24 hr) |
| --- | --- |
| 0 | 3113 |
| 2 | 2792 |
| 3 | 2335 |
| 5 | 2274 |
| 6 | 1865 |
| 7 | 2037 |
| 8 | 1851 |
| 9 | 1737 |

Figure 11:
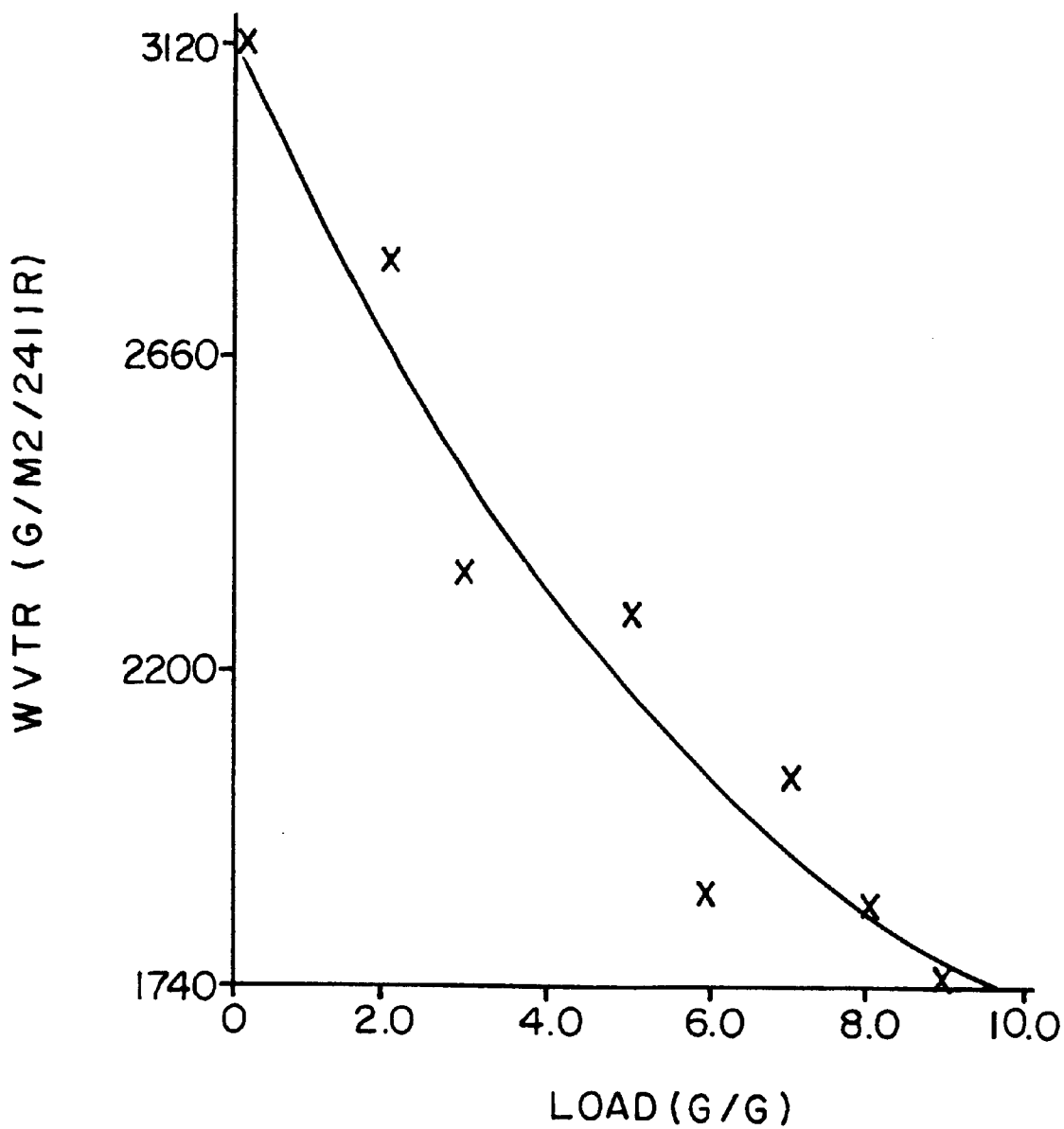
FIG. 11 is a graph which representatively shows water vapor transmission rate as a function of the amount of liquid loaded into an absorbent body.

The graph of FIG. 11 representatively shows the above data points correlated with a quadratic equation. From these data, it can be concluded that even a loading of 3 gm-fluid/gm-absorbent can reduce the WVTR of the absorbent composite to a level which may be insufficient to deliver a desired level of skin dryness. Preferably, the WVTR is at least about 3500 g/m$^2$ per 24 hr.

For the purposes of this Example, the WVTR test procedure is modified slightly to account for the liquid loaded into the absorbent composite: After filling the WVTR cup with 100 ml of distilled water and allowing it to equilibrate in the oven for one hour, the WVTR cup is weighed (without top/screws). Then, the screen and test sample are placed on the cup, and the top is screwed on. After loading the sample with synthetic urine and allowing it to equilibrate at room temperature for three minutes, the cup is placed in the oven per the ordinary procedure. Upon removal from the oven, the top, screen and sample are removed from the cup. The cup with remaining water is then weighed and the WVTR is determined.

EXAMPLE 20

Three samples of retention material were composed of fibrous coform material and superabsorbent particles. The retention material had a basis weight of about 900 gsm, a thickness of about 0.75 in (at 0.2 psi) and contained approximately 35 wt % superabsorbent. The samples exhibited the following characteristics:

| Sample No. | Moisture Retention Index |
|---|---|
| 1 | 92.95 |
| 2 | 92.06 |
| 3 | 89.53 |

EXAMPLE 21

Four samples were prepared with each sample comprising the retention material of Example 20, a layer of tissue on top of the retention material, a layer of HYDROFIL surge material on top of the tissue and a layer of Guilford loop material (19903) on top of the surge material. The tissue had basis weight of about 21 gsm and a thickness of about 0.009 in. The surge material had a basis weight of about 200 gsm and a thickness of about 0.086 in, and the Guilford loop material had a basis weight of about 108 gsm and a thickness of about 0.026 in. The samples of this Example exhibited the following characteristics:

| Sample No. | Moisture Retention Index | Wicking Index |
|---|---|---|
| 1 | 85.97 | 0.43 |
| 2 | 91.37 | 0.41 |
| 3 | 89.68 | 0.41 |
| 4 | 95.20 | — |

EXAMPLE 22

Four samples were prepared with each sample comprising a layer of tissue, a layer of HYDROFIL surge material on top of the tissue and a layer of Guilford loop material (19903) on top of the surge material. The tissue had basis weight of about 21 gsm and a thickness of about 0.009 in. The surge material had a basis weight of about 200 gsm and a thickness of about 0.086 in, and the Guilford loop material had a basis weight of about 108 gsm and a thickness of about 0.026 in. The samples of this Example exhibited the following characteristics:

| Sample No. | Moisture Retention Index | Wicking Index |
|---|---|---|
| 1 | 16.28 | 0.03 |
| 2 | 20.00 | 0.03 |
| 3 | 17.32* | 0.03 |
| 4 | 17.48 | — |

[*27 min reading]

EXAMPLE 23

Four samples were prepared with each sample comprising a layer of tissue, a layer of polyester fiberfill material on top of the tissue and a layer of Guilford loop material (19903) on top of the surge material. The tissue had basis weight of about 21 gsm and a thickness of about 0.009 in. The fiberfill material had a basis weight of about 180 gsm and a thickness of about 0.17 in, and the Guilford loop material had a basis weight of about 108 gsm and a thickness of about 0.026 in. The samples of this Example exhibited the following characteristics:

| Sample No. | Moisture Retention Index | Wicking Index |
|---|---|---|
| 1 | 11.58 | 0.02 |
| 2 | 17.17 | 0.02 |
| 3 | 12.35 | 0.01 |
| 4 | 13.68 | — |

Having thus described the invention in rather full detail, it will be readily apparent to a person of ordinary skill that various changes and modifications can be made without departing from the spirit of the invention. All of such changes and modifications are contemplated as being within the scope of the present invention, as defined by the subjoined claims.

We claim:

1. An absorbent article, which generally delimits a front waistband section, a rear waistband section and an intermediate section which interconnects said front and rear waistband sections, the article comprising:

a substantially vapor impermeable backsheet layer;

a liquid permeable topsheet layer positioned in facing relation with said backsheet layer;

an absorbent body for storing absorbed liquid, said absorbent body located between said backsheet layer and topsheet layer and including an absorbent material which provides for a level of moisture retention therein, said absorbent body having a humidity transfer zone portion wherein said humidity transfer zone portion comprises a substantially hydrophobic, nonwettable fibrous material which has an average basis weight within the range of about 5–300 gsm and a density of not more than about 0.1 gm/cc, said nonwettable fibrous material configured to limit a presence and wicking therein of liquid and to limit an occluding of said nonwettable fibrous material by liquid, said humidity transfer zone portion thereby exhibiting a relatively lower level of moisture retention as compared to other areas of said absorbent body where said liquid is normally stored; and a vapor permeable panel, which is substantially liquid impermeable and is connected to said backsheet layer in at least one of said waistband sections, said vapor permeable panel arranged in an operable adjacent registry with at least a portion of said nonwettable fibrous material of said humidity transfer zone portion to extend at least partially thereover, said connection of said vapor permeable panel to said backsheet layer and said registry of said vapor permeable panel with said humidity transfer zone portion arranged to allow movement of air into said nonwettable fibrous material through said vapor permeable panel.

2. An absorbent article as recited in claim 1, wherein said vapor permeable panel is composed of a material having a water vapor transmission rate (WVTR) value of at least about 2000 gm/sq.m/24 hr.

3. An absorbent article as recited in claims 1, wherein said vapor permeable panel provides a water vapor transmission rate value of at least about 4000 gm/sq.m/24 hr.

4. An absorbent article as recited in claim 1, wherein said vapor permeable panel provides a water vapor transmission rate value of at least about 5000 gm/sq.m/24 hr.

5. An absorbent article as recited in claim 1, further comprising at least one separation layer located between said topsheet layer and said absorbent body.

6. An absorbent article as recited in claim 5, wherein said at least one separation layer and said topsheet layer have a total combined bulk thickness (at 0.207 kPa) of at least about 0.078 cm.

7. An absorbent article as recited in claim 5, wherein said at least one separation layer and said topsheet layer have a total combined bulk thickness (at 0.207 kPa) within the range of about 0.1–0.6 cm.

8. An absorbent article as recited in claim 1, wherein said vapor permeable panel allows said movement of air over an area totaling at least about 5 sq. cm.

9. An absorbent article as recited in claim 1, wherein said vapor permeable panel is formed in said front waistband section of said backsheet layer.

10. An absorbent article as recited in claim 1, wherein said vapor permeable panel is formed in said rear waistband section of said backsheet layer.

11. An absorbent article as recited in claim 1, wherein said vapor permeable panel is formed in each of said front waistband section and said rear waistband section of said backsheet layer.

12. An absorbent article as recited in claim 1, wherein said vapor permeable panel comprises a calendered, meltblown, nonwoven fibrous web.

13. An absorbent article as recited in claim 1, wherein said nonwettable fibrous material in said humidity transfer zone portion comprises a mass of polyester fibers.

14. An absorbent article as recited in claim 1, wherein said nonwettable fibrous material has a Moisture Retention Index of not more than about 40 gm.

15. An absorbent article as recited in claim 1, wherein said nonwettable fibrous material has a Moisture Retention Index of not more than about 30 gm.

16. An absorbent article as recited in claim 1, wherein said nonwettable fibrous material has a Moisture Retention Index of not more than about 20 gm.

17. An absorbent article as recited in claim 1, wherein said nonwettable fibrous material has a Wicking Index of not more than about 0.2 gm.

18. An absorbent article as recited in claim 1, wherein said nonwettable fibrous material has a Wicking Index of not more than about 0.1 gm.

19. An absorbent article as recited in claim 1, wherein said nonwettable fibrous material has a Wicking Index of not more than about 0.05 gm.

20. An absorbent article as recited in claim 1, wherein said nonwettable fibrous material comprises a composite.

21. An absorbent article as recited in claim 1, wherein said nonwettable fibrous material comprises a multi-layer composite.

22. An absorbent article as recited in claim 1, wherein said nonwettable fibrous material has a density within the range of about 0.001–0.05 g/cc.

23. An absorbent article as recited in claim 1, wherein said vapor permeable panel is constructed of a material which provides a Test Relative Humidity (TRH) value of not more than about 80%.

24. An absorbent article as recited in claim 1, wherein said vapor permeable panel is constructed of a material which provides a TRH value of not more than about 75%.

25. An absorbent article as recited in claim 1, further comprising spacing means located between said topsheet layer and said absorbent body, said spacing means providing for effective fluid transfer between said topsheet layer and said absorbent body, said spacing means composed of substantially hydrophobic material, and said spacing means and topsheet layer having a combined bulk thickness of at least about 0.078 cm (measured at 0.207 kPa).

26. An absorbent article as recited in claim 25, wherein said spacing means comprises at least one separation layer composed of fibrous material, said at least one separation layer having a total bulk thickness of at least about 0.04 cm (measured dry at 0.207 kPa).

27. An absorbent article as recited in claim 26, wherein said at least one separation layer is composed of a knit fabric.

28. An absorbent article, comprising:

a front waistband section, a rear waistband section and an intermediate section which interconnects said front and rear waistband sections;

a substantially vapor impermeable backsheet layer;

a liquid permeable topsheet layer positioned in facing relation with said backsheet layer;

an absorbent body for storing absorbed liquid, said absorbent body located between said backsheet layer and topsheet layer and including an absorbent material which provides for a level of moisture retention therein, said absorbent body having a humidity transfer zone portion wherein said humidity transfer zone portion comprises a substantially hydrophobic, nonwettable fibrous material which has an average basis weight within the range of about 5–300 gsm and a density of not more than about 0.1 gm/cc, said nonwettable fibrous material configured to limit a presence and wicking therein of liquid and to limit an occluding of said nonwettable fibrous material by liquid, said humidity transfer zone portion thereby exhibiting a relatively lower level of moisture retention as compared to other areas of said absorbent body where said liquid is normally stored; and spacing means including at least one separation layer located between said topsheet layer and said absorbent body, said at least one separation layer providing for effective fluid transfer between said topsheet layer and said absorbent body, and said spacing means composed of substantially hydrophobic material and having a total bulk thickness within a range of about 0.07–0.51 cm (measured dry at 0.207 kPa); and a vapor permeable panel, which is substantially liquid impermeable and is connected to said backsheet layer in at least one of said waistband sections of said article, said vapor permeable panel arranged in an operable adjacent registry with at least a portion of said nonwettable fibrous material of said humidity transfer zone portion to extend at least partially thereover, said connection of said vapor permeable panel to said backsheet layer and said registry of said vapor permeable panel over said humidity transfer zone portion arranged to allow movement of air into said nonwettable fibrous material through said vapor permeable panel, and said vapor permeable panel arranged to allow said movement over an area within the range of about 5–400 sq. cm.

29. An absorbent article as recited in claim 28, wherein said vapor permeable panel material extends along about 10–40% of the length of said absorbent body.

30. An absorbent article as recited in claim 28, wherein said nonwettable fibrous material has a Moisture Retention Index of not more than about 40 gm.

31. An absorbent article as recited in claim 28, wherein said nonwettable fibrous material has a Moisture Retention Index of not more than about 30 gm.

32. An absorbent article as recited in claim 28, wherein said nonwettable fibrous material has a Moisture Retention Index of not more than about 20 gm.

33. An absorbent article as recited in claim 28, wherein said nonwettable fibrous material has a Wicking Index of not more than about 0.2 gm.

34. An absorbent article as recited in claim 28, wherein said nonwettable fibrous material has Wicking Index of not more than about 0.1 gm.

35. An absorbent article as recited in claim 28, wherein said nonwettable fibrous material has Wicking Index of not more than about 0.05 gm.

36. An absorbent article as recited in claim 28, wherein said nonwettable fibrous material has a density within the range of about 0.001–0.05 gm/cc.

37. An absorbent article as recited in claim 28, wherein said nonwettable fibrous material has a bulk thickness of at least about 0.51 cm (measured dry at 1.38 kPa).

38. An absorbent article, which generally delimits a front waistband section, a rear waistband section and an intermediate section which interconnects said front and rear waistband sections, the article comprising:

a substantially vapor impermeable backsheet layer;

a liquid permeable topsheet layer positioned in facing relation with said backsheet layer;

an absorbent body for storing absorbed liquid, said absorbent body located between said backsheet layer and topsheet layer and including an absorbent material which provides for a level of moisture retention therein, said absorbent body having a humidity transfer zone portion wherein said humidity transfer zone portion comprises a substantially hydrophobic, nonwettable fibrous material which has an average basis weight within the range of about 5–300 gsm and a density within the range of about 0.001–0.05 gm/cc, said nonwettable fibrous material configured to limit a presence and wicking therein of liquid and to limit an occluding of said nonwettable fibrous material by liquid, said humidity transfer zone portion thereby exhibiting a relatively lower level of moisture retention as compared to other areas of said absorbent body where said liquid is normally stored;

at least one liquid permeable separation layer located between said topsheet layer and said absorbent body, said at least one separation layer allowing fluid transfer between said topsheet layer and said absorbent body, said at least one separation layer composed of substantially hydrophobic material, and said at least one separation layer and top sheet layer having a combined bulk thickness of at least about 0.078 cm (at 0.207 kPa); and a vapor permeable panel, which is substantially liquid impermeable and is connected to said backsheet layer at at least one of said waistband sections of said article, said vapor permeable panel arranged in an operable adjacent registry with at least a portion of said nonwettable fibrous material of said humidity transfer zone portion to extend at least partially thereover, said connection of said vapor permeable panel to said backsheet layer and said registry of said vapor permeable panel over said humidity transfer zone portion arranged to allow movement of air into said nonwettable fibrous material through said vapor permeable panel, said vapor permeable panel comprising a calendered composite fibrous web which includes a barrier layer composed of meltblown fibers bonded to a reinforcing layer, said reinforcing layer having a grab tensile strength within the range of about 1500–10,000 grams/inch.

39. An absorbent article as recited in claim 38, wherein said vapor permeable panel is composed of a material having a water vapor transmission rate (WVTR) value of at least about 2000 gm/sq.m/24 hr.

40. An absorbent article as recited in claim 38, wherein said at least one separation layer has a total bulk thickness of at least about 0.04 cm (measured dry at 0.207 kPa).

41. An absorbent article as recited in claim 38, wherein said at least one separation layer and said topsheet layer have a total combined bulk thickness (at 0.207 kPa) within the range of about 0.1–0.6 cm.

42. An absorbent article as recited in claim 38, wherein said vapor permeable panel allows said movement of air over an area totaling at least about 5 sq. cm.

43. An absorbent article as recited in claim 38, wherein said vapor permeable panel is formed in said front waistband section of said backsheet layer.

44. An absorbent article as recited in claim 38, wherein said at least one separation layer comprise 1–5 layers of a nonwoven fibrous web material.

45. An absorbent article as recited in claim 44, wherein said nonwoven fibrous web material is a layer of spunbond fibrous web material composed of polyolefin fibers.

46. An absorbent article as recited in claim 45, wherein said at least one separation layer provides a combined effective basis weight of at least about 34 gsm.

47. An absorbent article as recited in claim 45, wherein said at least one separation layer is composed of polypropylene fibers and has a combined effective basis weight within the range of about 55–170 gsm and an effective bulk density of about 0.03–0.5 g/cc (at 0.207 kPa).

48. An absorbent article as recited in claim 47, wherein said polypropylene fibers have a denier within the range of about 1.5–6 d.

49. An absorbent article as recited in claim 38, wherein said absorbent body has a plurality of apertures through a thickness thereof and wherein at least a portion of said apertures have said nonwettable fibrous material located therein and are in operable registration with said vapor permeable panel.

50. An absorbent article as recited in claim 30, wherein said vapor permeable panel is constructed of a material which provides a Test Relative Humidity (TRH) value of not more than about 80%.

51. An absorbent article as recited in claim 38, wherein said vapor permeable panel is constructed of a material which provides a TRH value of not more than about 75%.

52. An absorbent article as recited in claim 38, wherein said at least one separation layer is limited to a front two-thirds section of said absorbent article.

53. An absorbent article as recited in claim 38, wherein said at least one separation layer is limited to a middle 35–60% section of said absorbent article.

54. An absorbent article as recited in claim 38, wherein said article comprises a plurality of individual separation layers, two or more of which are connected together at selected spaced locations.

55. An absorbent article as recited in claim 54, wherein said separation layers are connected together at discrete locations arranged in a selected pattern.

56. An absorbent article, comprising a front waistband section, a rear waistband section and an intermediate section which interconnects said front and rear waistband sections;

a substantially vapor impermeable backsheet layer;

a liquid permeable topsheet layer positioned in facing relation with said backsheet layer;

an absorbent body for storing absorbed liquid, said absorbent body located between said backsheet layer and topsheet layer and including an absorbent material which provides for a level of moisture retention therein, said absorbent body having a humidity transfer zone portion wherein said humidity transfer zone portion comprises a substantially hydrophobic, nonwettable fibrous material which has an average basis weight of not more than about 550 gsm, said nonwettable fibrous material configured to limit a presence and wicking therein of liquid and to limit an occluding of said humidity transfer zone portion by held liquid, said humidity transfer zone portion thereby exhibiting a relatively lower level of moisture retention as compared to other areas of said absorbent body where said liquid is normally stored;

spacing means located between said topsheet layer and said absorbent body, said spacing means providing for effective fluid transfer between said topsheet layer and said absorbent body, and said spacing means composed of substantially hydrophobic material and having a total bulk thickness of at least about 0.04 cm (measured dry at 0.207 kPa); and a vapor permeable panel, which is substantially liquid impermeable and is connected to extend from said backsheet layer at a waistband section of said article, said panel arranged in an overlying registry with at least a portion of said nonwettable fibrous material of said humidity transfer zone portion to extend at least partially thereover, said connection of said vapor permeable panel to said backsheet layer and said registry of said vapor permeable panel over said humidity transfer zone portion arranged to allow movement of air into said nonwettable fibrous material through said vapor permeable panel.

57. An absorbent article as recited in claim 56, wherein said vapor permeable panel is composed of a material which has a water vapor transmission rate (WVTR) of at least about 2000 gm/sq.m/24 hr.

58. An absorbent article as recited in claim 56, wherein said vapor permeable panel extends over an area within the range of about 5–400 sq. cm.

59. An absorbent article as recited in claim 56, wherein said vapor permeable panel material extends along about 10–40% of the length of said absorbent body beginning from a front waistband, terminal edge of said absorbent body.

60. An absorbent article as recited in claim 56, wherein said nonwettable fibrous material has a density of not more than about 0.1 g/cc and an average basis weight within the range of about 5–300 gsm.

61. An absorbent article, comprising:
a front waistband section, a rear waistband section, and an intermediate section which interconnects said front and rear waistband sections;
a substantially vapor impermeable backsheet layer;
a liquid permeable topsheet layer positioned in facing adjacent relation with said backsheet layer;
a vapor permeable panel connected to said backsheet layer in at least one of said waistband sections of said article, said vapor permeable panel composed of a material which is substantially liquid impermeable and has a water vapor transmission rate (WVTR) of at least about 2000 gm/sq.m/24 hr; and
an absorbent body for storing liquid, said absorbent body having a basis weight within the range of about 400–1200 gsm and including a humidity transfer zone portion which comprises a substantially hydrophobic, nonwettable fibrous material having an average basis weight within the range of about 5–300 gsm and a density within the range of about 0.001–0.05 gm/cc, said nonwettable fibrous material configured to limit a presence and wicking therein of liquid and to limit an occluding of said nonwettable fibrous material by liquid, said humidity transfer zone portion thereby exhibiting a relatively lower level of moisture retention as compared to other areas of said absorbent body where said liquid is normally stored, said absorbent body located between said backsheet layer and topsheet layer and arranged with at least a portion of said nonwettable fibrous material in an underlying, operably adjacent, facing registry with said vapor permeable panel, said connection of said vapor permeable panel to said backsheet layer and said registry of said vapor permeable panel with said humidity transfer zone portion arranged to allow movement of air into said nonwettable fibrous material through said vapor permeable panel over a panel area of at least about 22 sq. cm.

62. An absorbent article as recited in claim 61, wherein said vapor permeable panel extends over an area of at least about 45 sq. cm.

63. An absorbent article, comprising:
a front waistband section, a rear waistband section, and an intermediate section which interconnects said front and rear waistband sections;
a substantially vapor impermeable backsheet layer;
a liquid permeable topsheet layer positioned in facing adjacent relation with said backsheet layer;
a vapor permeable panel which is substantially liquid impermeable and is connected to said backsheet layer in at least one of said waistband sections said vapor permeable panel composed of a material having a water vapor transmission rate (WVTR) of at least about 2000 gm/sq.m/24 hr.; and
an absorbent body for storing absorbed liquid, said absorbent body located between said backsheet layer and topsheet layer and including an absorbent material which provides for a level of moisture retention therein,
said absorbent body having a humidity transfer zone portion wherein said humidity transfer zone portion comprises a substantially hydrophobic, nonwettable fibrous material having an average basis weight within the range of about 5–300 gsm and a density within the range of about 0.001–0.05 gm/cc,
said nonwettable fibrous material configured to limit a presence and wicking therein of liquid and to limit an occluding of said nonwettable fibrous material by liquid, and said nonwettable fibrous material located in one or more apertures formed through the absorbent body, said humidity transfer zone portion thereby exhibiting a relatively lower level of moisture retention as compared to other areas of said absorbent body where said liquid is normally stored,
said humidity transfer zone portion is located in an operably adjacent, facing registration with said vapor permeable panel,
said one or more apertures and nonwettable fibrous material provide for a Frazier air porosity value of at least about 15.25 m$^3$/min/m$^2$, and
said connection of said vapor permeable panel to said backsheet layer and said registration of said humidity transfer zone portion with said vapor permeable panel arranged to allow movement of air into said nonwettable fibrous material through said vapor permeable panel over a panel area of at least about 22 sq. cm.

64. An absorbent article as recited in claim 63, wherein said one or more apertures and nonwettable fibrous material provide for a Frazier air porosity value within the range of about 15.25–30 m³/min/m².

65. An absorbent article as recited in claim 63, wherein said one or more apertures are substantially circular and have an average diameter within the range of about 0.5–2.0 cm.

66. An absorbent article as recited in claim 38, wherein said barrier layer has a basis weight within the range of about 10–50 gsm and said reinforcing layer has a basis weight within the range of about 0–35 gsm.

67. An absorbent article as recited in claim 66, wherein said barrier layer is composed of polymer fibers having an average cross-sectional diameter of about 3.0 micrometers or less.

68. An absorbent article, which generally delimits a front waistband section a rear waistband section and an intermediate section which interconnects said front and rear waistband sections, the article comprising:

a substantially vapor impermeable backsheet layer;

a liquid permeable topsheet layer positioned in facing relation with said backsheet layer;

an absorbent body for storing absorbed liquid, said absorbent body located between said backsheet layer and topsheet layer and including an absorbent material which provides for a level of moisture retention therein, said absorbent body having a humidity transfer zone portion wherein said humidity transfer zone portion comprises a substantially hydrophobic, nonwettable fibrous material having an average basis weight within the range of about 5–300 gsm located in one or more apertures which are entirely spaced from longitudinally opposed waistband edges of said absorbent body and are formed through said absorbent body, said nonwettable fibrous material configured to limit a presence and wicking therein of liquid and to limit an occluding of said nonwettable fibrous material by liquid, said humidity transfer zone portion thereby exhibiting a relatively lower level of moisture retention as compared to other areas of said absorbent body where said liquid is normally stored; and a vapor permeable panel, which is substantially liquid impermeable and is connected to said backsheet layer in at least one of said waistband sections, said vapor permeable panel arranged in an operable adjacent registry with at least a portion of said nonwettable fibrous material of said humidity transfer zone portion to extend at least partially thereover, said connection of said vapor permeable panel to said backsheet layer and said registry of said vapor permeable panel with said humidity transfer zone portion arranged to allow movement of air into said nonwettable fibrous material through said vapor permeable panel.

69. An absorbent article, which generally delimits a front waistband section, a rear waistband section and an intermediate section which interconnects said front and rear waistband sections, the article comprising:

a substantially vapor impermeable backsheet layer;

a liquid permeable topsheet layer positioned in facing relation with said backsheet layer;

an absorbent body for storing absorbed liquid, said absorbent body located between said backsheet layer and topsheet layer and including an absorbent material which provides for a level of moisture retention therein, said absorbent body having a humidity transfer zone portion wherein said humidity transfer zone portion comprises a substantially hydrophobic, nonwettable fibrous material which has an average basis weight within the range of about 5–300 gsm and is configured to span across an entire waistband edge of said absorbent body, said nonwettable fibrous material configured to limit a presence and wicking therein of liquid and to limit an occluding of said nonwettable fibrous material by liquid, said humidity transfer zone portion thereby exhibiting a relatively lower level of moisture retention as compared to other areas of said absorbent body where said liquid is normally stored; and a vapor permeable panel, which is substantially liquid impermeable and is connected to said backsheet layer in at least one of said waistband sections, said vapor permeable panel arranged in an operable adjacent registry with at least a portion of said nonwettable material of said humidity transfer zone portion to extend at least partially thereover, said connection of said vapor permeable panel to said backsheet layer and said registry of said vapor permeable panel with said humidity transfer zone portion arranged to allow movement of air into said nonwettable fibrous material through said vapor permeable panel.

* * * * *

UNITED STATES PATENT AND TRADEMARK OFFICE
CERTIFICATE OF CORRECTION

| | | |
|---|---|---|
| PATENT NO. | : 6,316,687 B1 | Page 1 of 1 |
| DATED | : November 13, 2001 | |
| INVENTOR(S) | : James Arthur Davis et al. | |

It is certified that error appears in the above-identified patent and that said Letters Patent is hereby corrected as shown below:

Column 37,
Line 12, delete "0-35" and substitute -- 10-35 --.

Signed and Sealed this

Twenty-fifth Day of February, 2003

JAMES E. ROGAN
*Director of the United States Patent and Trademark Office*